United States Patent

Yoshida et al.

[11] Patent Number: 5,726,325
[45] Date of Patent: Mar. 10, 1998

[54] TRICYCLIC COMPOUNDS

[75] Inventors: Makoto Yoshida; Shin-ichi Sasaki, both of Shizuoka; Shigeru Aono, Numazu; Shigeki Fujiwara, Mishima; Haruki Takai, Shizuoka; Tsuyoshi Yamagata, Shizuoka; Ken Nagashima, Shizuoka; Akira Karasawa, Shizuoka, all of Japan

[73] Assignee: Kyowa Hakko Kogyo Co., Ltd., Tokyo, Japan

[21] Appl. No.: 849,399

[22] PCT Filed: Oct. 16, 1996

[86] PCT No.: PCT/JP96/02997

§ 371 Date: Jun. 6, 1997

§ 102(e) Date: Jun. 6, 1997

[87] PCT Pub. No.: WO97/14672

PCT Pub. Date: Apr. 24, 1997

[30] Foreign Application Priority Data

Oct. 16, 1995 [JP] Japan ................... 7-267232
Dec. 13, 1995 [JP] Japan ................... 7-324298

[51] Int. Cl.[6] .................. C07D 313/02; C07D 333/80
[52] U.S. Cl. .................. 549/48; 549/354; 549/12; 549/13; 549/458; 546/89; 546/80; 546/93; 568/326
[58] Field of Search .................. 549/48, 354

[56] References Cited

U.S. PATENT DOCUMENTS 4,477,465  10/1984  Martin et al. .................. 424/275
5,116,863  5/1992   Oshima et al. .................. 514/450
5,272,163  12/1993  Russell et al. .................. 514/347

FOREIGN PATENT DOCUMENTS 0524781  1/1993  European Pat. Off. .

OTHER PUBLICATIONS

J. Med. Chem., vol. 39, No. 23 (Nov. 1996) pp. 4592–4601.

*Primary Examiner*—Johann Richter
*Assistant Examiner*—Laura L. Stockton
*Attorney, Agent, or Firm*—Fitzpatrick, Cella, Harper & Scinto

[57] ABSTRACT

The present invention relates to tricyclic compounds represented by general formula (I) which are useful as therapeutic agents for urinary incontinence:

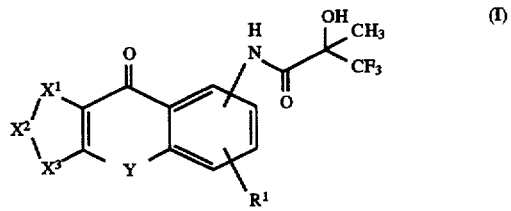

wherein $R^1$ represents hydrogen and the like; $-X^1-X^2-X^3-$ represents $-CR^2=CR^3-CR^4=CR^5-$ (wherein $R^2$, $R^3$, $R^4$, and $R^5$ represent hydrogen and the like) and the like; and Y represents $-CH_2O-$ and the like.

3 Claims, No Drawings

TRICYCLIC COMPOUNDS

This application is a 371 of PCT/JP96/02997 filed Oct. 16, 1996.

TECHNICAL FIELD

The present invention relates to tricyclic compounds which are useful as therapeutic agents for urinary incontinence.

BACKGROUND ART

Japanese Published Unexamined Patent Application No. 286915/93 discloses N-substituted propanamide derivatives which are useful for the treatment of urinary incontinence.

DISCLOSURE OF THE INVENTION

The present invention relates to tricyclic compounds represented by general formula (I):

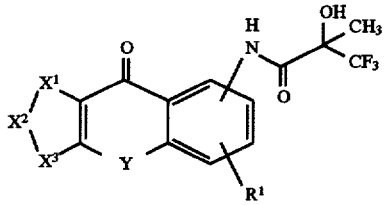

wherein $R^1$ represents hydrogen, lower alkyl, lower alkoxy, or halogen; —$X^1$—$X^2$—$X^3$— represents —$CR^2$=$CR^3$—$CR^4$=$CR^5$— (wherein $R^2$, $R^3$, $R^4$, and $R^5$, which may be the same or different, each represents hydrogen, lower alkyl, lower alkoxy, or halogen), —$CR^2$=$CR^3$—$CR^4$=N— (wherein $R^2$, $R^3$, and $R^4$ have the same significances as defined above), —$CR^2$=$CR^3$—S— (wherein $R^2$ and $R^3$ have the same significances as defined above), —$CR^2$=$CR^3$—O— (wherein $R^2$ and $R^3$ have the same significances as defined above), —S—$CR^4$=$CR^5$— (wherein $R^4$ and $R^5$ have the same significances as defined above), or —O—$CR^4$=$CR^5$— (wherein $R^4$ and $R^5$ have the same significances as defined above); and Y represents —$CH_2O$—, —$CH_2S$—, —$CH_2SO$—, —CH=CH—, or —$(CH_2)_n$— (wherein n represents 0, 1, or 2) [which are hereinafter referred to as Compound (I), and the same applies to the compounds of other formula numbers].

In the definitions of the groups in general formula (I), the lower alkyl and the lower alkyl moiety of the lower alkoxy mean a straight-chain or branched alkyl group having 1 to 6 carbon atoms, such as methyl, ethyl, propyl, isopropyl, butyl, isobutyl, sec-butyl, tert-butyl, pentyl, and hexyl. The halogen includes fluorine, chlorine, bromine, and iodine.

The processes for preparing Compound (I) are described below.

Step 1

Compound (I) can be prepared according to the following reaction step.

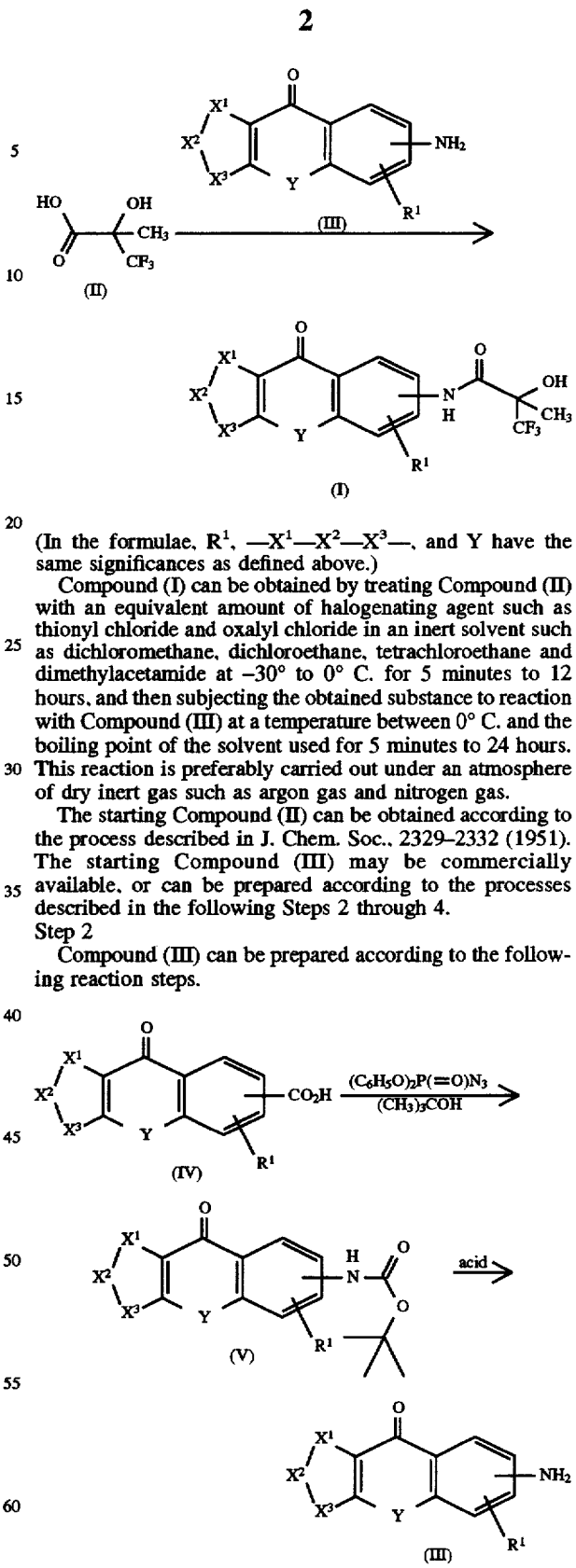

(In the formulae, $R^1$, —$X^1$—$X^2$—$X^3$—, and Y have the same significances as defined above.)

Compound (I) can be obtained by treating Compound (II) with an equivalent amount of halogenating agent such as thionyl chloride and oxalyl chloride in an inert solvent such as dichloromethane, dichloroethane, tetrachloroethane and dimethylacetamide at −30° to 0° C. for 5 minutes to 12 hours, and then subjecting the obtained substance to reaction with Compound (III) at a temperature between 0° C. and the boiling point of the solvent used for 5 minutes to 24 hours. This reaction is preferably carried out under an atmosphere of dry inert gas such as argon gas and nitrogen gas.

The starting Compound (II) can be obtained according to the process described in J. Chem. Soc., 2329–2332 (1951). The starting Compound (III) may be commercially available, or can be prepared according to the processes described in the following Steps 2 through 4.

Step 2

Compound (III) can be prepared according to the following reaction steps.

(In the formulae, $R^1$, —$X^1$—$X^2$—$X^3$—, and Y have the same significances as defined above.)

The starting Compound (IV) can be obtained according to the known methods [J. Med. Chem., 19, 941 (1976); ibid., 20, 66 (1977); ibid., 20, 1499 (1977); ibid., 20, 1557 (1977); ibid., 21, 633 (1978); ibid., 22, 1357 (1979); ibid., 27, 372 (1984); ibid., 29, 2347 (1986); ibid., 29, 2074 (1992); ibid., 38, 496 (1995), etc.] or similar methods thereto.

Compound (V) can be obtained by treating Compound (IV) according to the methods described in Synthesis, 295 (1990), etc. in tert-butanol in the presence of an equivalent amount of diphenylphosphoryl azide under an atmosphere of dry inert gas such as argon gas and nitrogen gas.

Compound (III) can be obtained by hydrolyzing Compound (V) in an appropriate solvent such as trifluoroacetic acid, hydrochloric acid/dioxane and hydrobromic acid/acetic acid at a temperature between 0° C. and the boiling point of the solvent used for 1 to 24 hours.

Step 3

Compound (IIIa), which is Compound (III) in which Y is —CH$_2$O—, can also be prepared according to the following reaction steps.

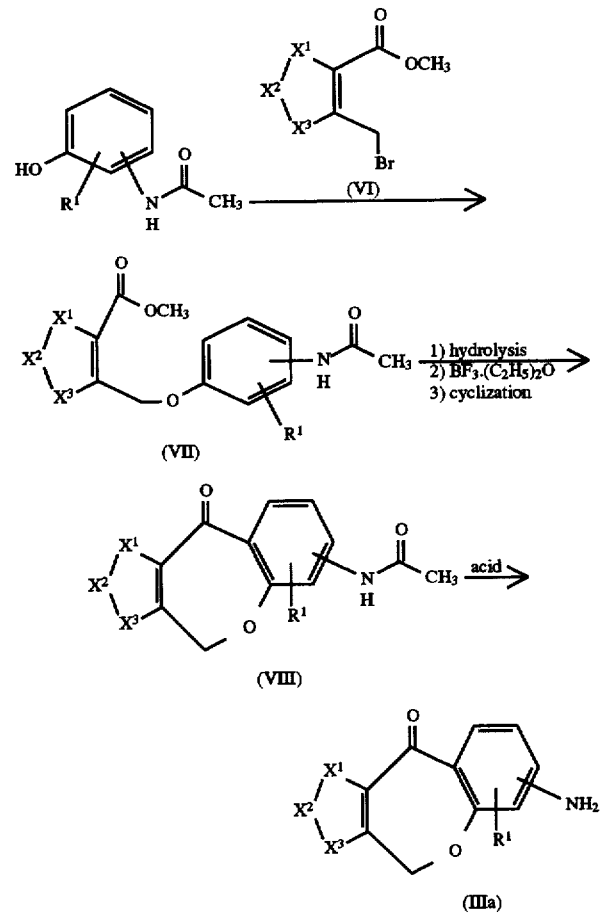

(In the formulae, $R^1$ and —$X^1$—$X^2$—$X^3$— have the same significances as defined above.)

The starting Compound (VI) can be obtained by heating under reflux the corresponding starting material which is commercially available such as methyl 2-methylbenzoate and methyl 2-methylnicotinate in a solvent such as carbon tetrachloride in the presence of a radical initiator such as azobisisobutyronitrile (AIBN) and an equivalent amount of a brominating agent such as N-bromosuccinimide (NBS) for 1 to 24 hours according to a known method.

Compound (VII) can be obtained by reacting Compound (VI) with commercially available acetamidophenol such as 3-acetamidophenol in an inert solvent such as tetrahydrofuran, dimethylformamide, dimethylacetamide and dimethyl sulfoxide in the presence of an appropriate base such as cesium carbonate at a temperature between 0° C. and the boiling point of the solvent used for 1 to 24 hours.

Compound (VIII) can be obtained by hydrolyzing Compound (VII) in a mixed solvent of water and a solvent such as methanol, ethanol, dioxane and tetrahydrofuran in the presence of an appropriate base such as lithium hydroxide, sodium hydroxide and potassium hydroxide at a temperature between room temperature and the boiling point of the solvent used for 1 to 24 hours; treating the obtained carboxylic acid with an equivalent amount of trifluoroacetic anhydride in an inert solvent such as dichloromethane, tetrahydrofuran, dimethylformamide, dimethylacetamide and dimethyl sulfoxide at a temperature between −15° C. and room temperature according to a known method (Japanese Published Unexamined Patent Application No. 91040/90 etc.) to give acid anhydride; and then without isolation subjecting the obtained acid anhydride to ring closure reaction in the same solvent in the presence of 0.1 to one equivalent of Lewis acid such as boron trifluoride diethyl etherate at a temperature between 0° C. and the boiling point of the solvent used.

Compound (IIIa) can be obtained by heating Compound (VIII) under reflux in concentrated hydrochloric acid etc.

Compound (IIIb), which is Compound (III) in which Y is —CH$_2$S—, can also be obtained according to the method similar to that in Step 3 except for using acetamidothiophenol such as 3-acetamidothiophenol instead of acetamidophenol.

Step 4

Compound (IIIc), which is Compound (III) in which Y is —(CH$_2$)$_2$—, and Compound (IIId), which is Compound (III) in which Y is —CH=CH—, can also be prepared according to the following reaction steps.

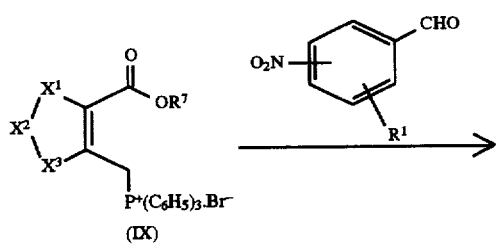

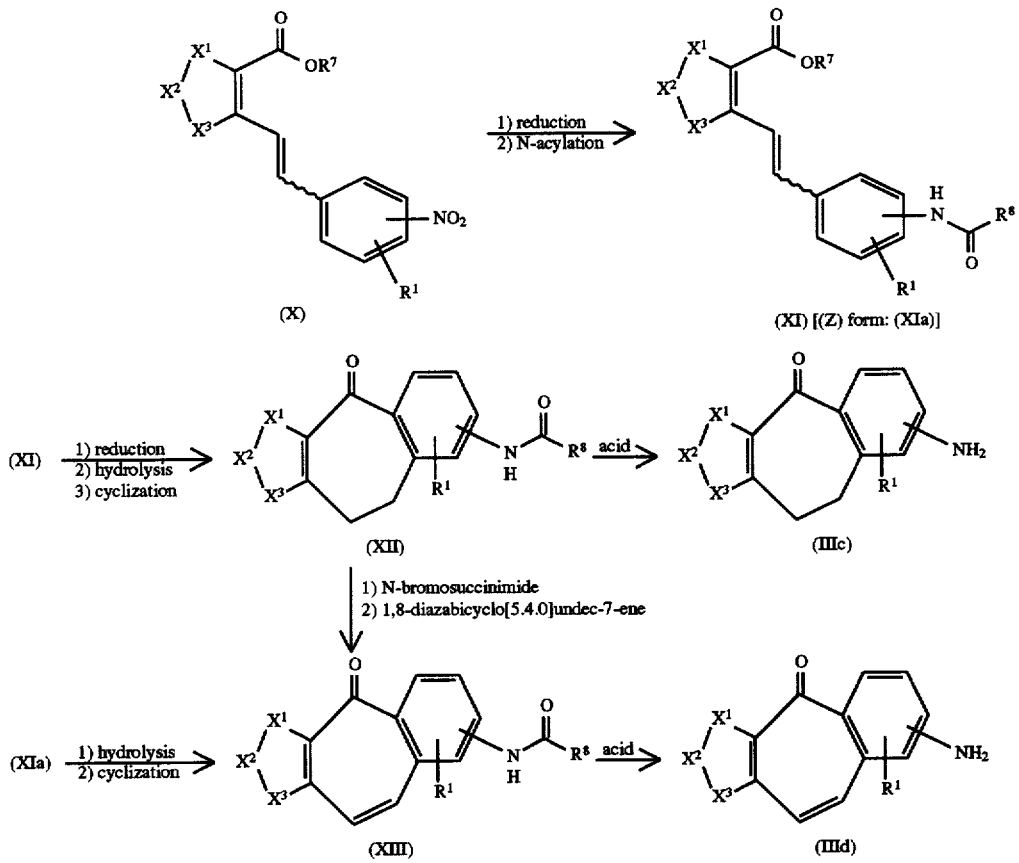

(In the formulae, R⁷ and R⁸ represent lower alkyl; and R¹ and —X¹—X²—X³— have the same significances as defined above.)

In the definitions of R⁷ and R⁸, the lower alkyl has the same significance as the lower alkyl defined above.

The starting Compound (IX) can be obtained by reacting Compound (VI) with an equivalent amount of triphenylphosphine in a solvent such as toluene at a temperature between 0° C. and the boiling point of the solvent used for 1 to 24 hours according to a known method.

Compound (X) can be obtained by reacting Compound (IX) with commercially available nitrobenzaldehyde such as 3-nitrobenzaldehyde in an inert solvent such as tetrahydrofuran, dioxane and ether in the presence of an appropriate base such as sodium hydride, potassium tert-butoxide and potassium carbonate at a temperature between 0° C. and the boiling point of the solvent used for 1 to 24 hours.

Compound (XI) can be obtained as an E/Z mixture by reducing Compound (X) with an appropriate reducing agent such as reduced iron in a mixed solvent of water and a solvent such as methanol and ethanol at a temperature between room temperature and the boiling point of the solvent used for 1 to 24 hours, and then reacting the obtained amine with an acylating agent such as acetic anhydride and acetyl chloride in an inert solvent such as dichloromethane, tetrahydrofuran, dioxane and dimethylformamide in the presence of a base such as triethylamine and diisopropylethylamine at a temperature between 0° C. and the boiling point of the solvent used for 1 to 24 hours.

Compound (XII) can be obtained by subjecting Compound (XI) to catalytic reduction with hydrogen in a solvent such as methanol, ethanol, dioxane and tetrahydrofuran in the presence of an appropriate catalyst such as palladium and platinum at a temperature between room temperature and the boiling point of the solvent used for 1 to 24 hours, hydrolyzing the reduction product according to the method similar to that in Step 3 to give a carboxylic acid, and then subjecting the obtained carboxylic acid to ring closure reaction according to the method similar to that in Step 3.

Compound (IIIc) can be obtained by heating Compound (XII) under reflux in concentrated hydrochloric acid etc.

Compound (XIII) can be obtained by hydrolyzing Compound (XIa), which is Z-form within Compound (XI), according to the method similar to that in Step 3 to give a carboxylic acid, and then subjecting the obtained carboxylic acid to ring closure reaction according to the method similar to that in Step 3.

Compound (IIId) can be obtained by heating Compound (XIII) under reflux in concentrated hydrochloric acid etc.

Compound (IIId) can also be prepared according to the known methods [J. Med. Chem., 20, 1557 (1977) etc.] or similar methods thereto.

Compound (XIII) can be obtained by brominating Compound (XII) by heating it under reflux in a solvent such as carbon tetrachloride in the presence of a radical initiator such as AIBN and an equivalent amount of a brominating agent such as NBS for 1 to 24 hours, and then subjecting the obtained compound to dehydrobromination in an appropriate inert solvent such as dimethylformamide in the presence of 1,8-diazabicyclo[5.4.1]undec-7-ene (DBU) or the like at a temperature between room temperature and 120° C. Compound (IIId) can be obtained by hydrolyzing the obtained Compound (XIII) with an acid in the same manner as described above.

Compound (Ia), which is Compound (I) in which Y is —CH$_2$SO—, can be obtained by treating Compound (Ib), which is Compound (I) in which Y is —CH$_2$S—, with an equivalent amount of an oxidizing agent such as 3-chloroperbenzoic acid in a solvent such as dichloromethane at a temperature between 0° C. and the boiling point of the solvent used for 1 to 24 hours according to a known method.

The intermediates and the desired compounds in the processes described above can be isolated and purified by purification methods conventionally used in synthetic organic chemistry, for example, filtration, extraction, washing, drying, concentration, recrystallization, and various kinds of chromatography. The intermediates may be subjected to the subsequent reaction without purification. In the case where the intermediates are obtained in the form of an E/Z mixture and its separation is desired, it may be separated and purified by fractionation methods such as fractional crystallization, fractional precipitation, and fractional dissolution, various kinds of chromatography, and the like.

Compound (I) may exist in the form of adducts with water or various solvents, which are also within the scope of the present invention.

Representative examples of Compound (I) are shown below in Table 1.

TABLE 1

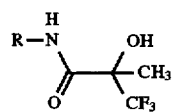

TABLE 1-continued
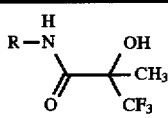
| Compd. No. | R | Compd. No. | R |
|---|---|---|---|
| 11 | 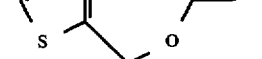 | 18 | |
| 12 | | 19 | |
| 13 | | 20 | |
| 14 | | 21 | |
| 15 | | 22 | |
| 16 | | 23 | |
| 17 | | 24 | |

TABLE 1-continued
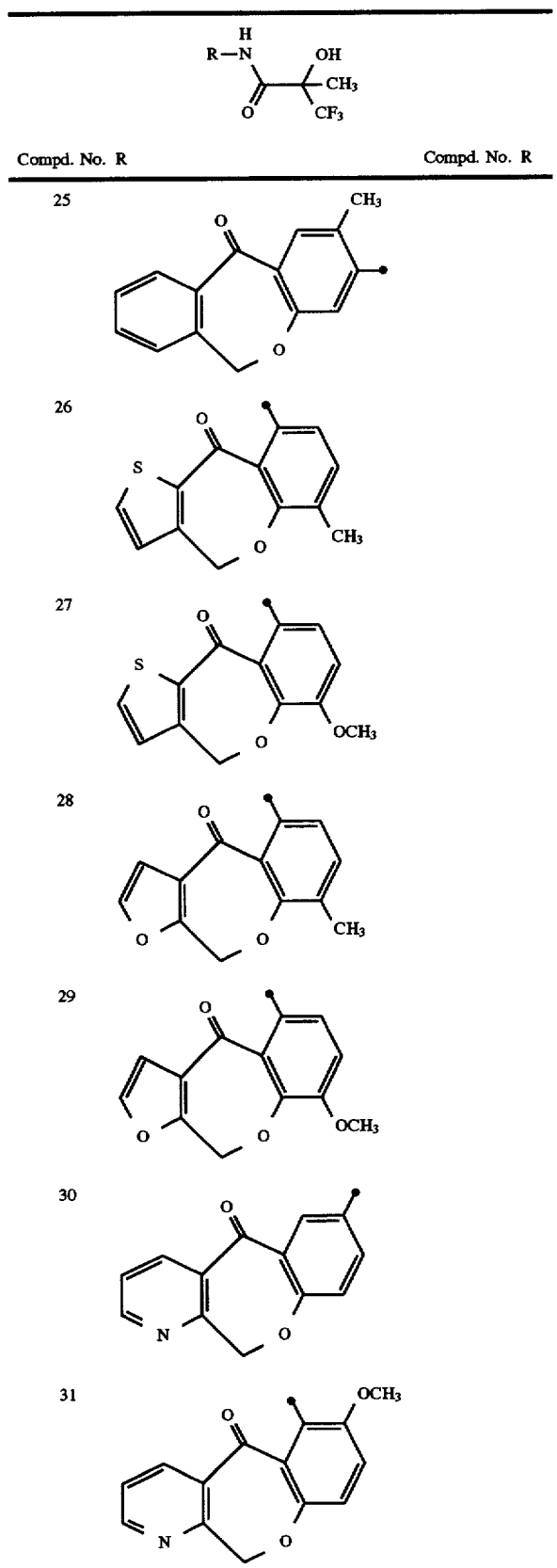
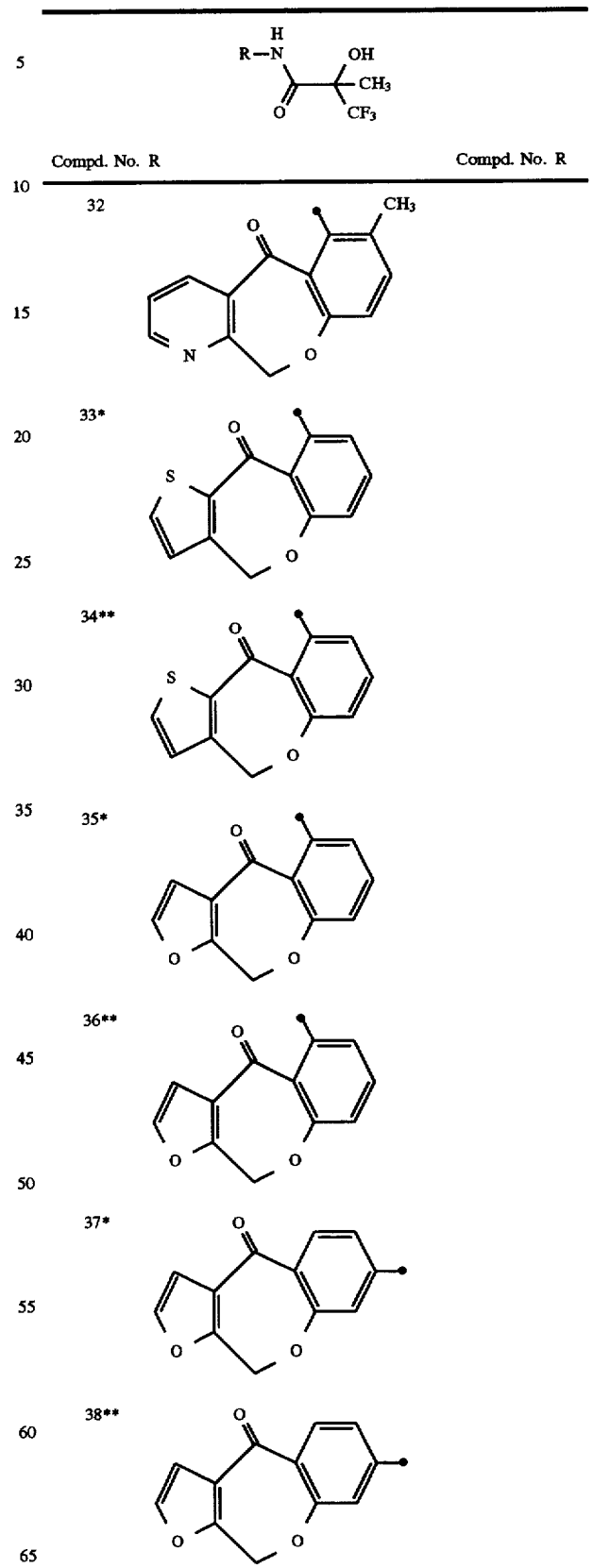

TABLE 1-continued $$R-\underset{H}{N}-\underset{O}{\overset{OH}{\underset{CF_3}{C}}}-CH_3$$

| Compd. No. | R |
|---|---|
| 39* | (structure) |
| 40 | (structure) |
| 41 | (structure) |
| 42 | (structure) |
| 43 | (structure) |
| 44 | (structure) |
| 45 | (structure) |
| 46 | (structure) |
| 47 | (structure) |
| 48 | (structure) |
| 49 | (structure) |
| 50 | (structure) |
| 51 | (structure) |
| 52 | (structure) |

TABLE 1-continued

R—NH—C(=O)—C(OH)(CH₃)(CF₃)

| Compd. No. | R |
|---|---|
| 53 | dibenzosuberone (6,11-dihydro-5H-dibenzo[a,d]cyclohepten-5-one) derivative |
| 54 | dibenzosuberone derivative |
| 55 | thieno-benzo cycloheptanone derivative |
| 56 | thieno-benzo cycloheptanone derivative |
| 57 | dithieno cycloheptanone derivative |
| 58 | furo-benzo cycloheptanone derivative |
| 59 | pyrido-benzo cycloheptanone derivative |
| 60 | dibenzo[a,d]cyclohepten-5-one derivative |
| 61 | dibenzo[a,d]cyclohepten-5-one derivative |
| 62 | dibenzo[a,d]cyclohepten-5-one derivative |
| 63 | thieno-benzo cycloheptenone derivative |
| 64 | thieno-benzo cycloheptenone derivative |
| 65 | thieno-benzo cycloheptenone derivative |
| 66 | dithieno cycloheptenone derivative |

TABLE 1-continued

R—NH—C(=O)—C(OH)(CH₃)(CF₃)

| Compd. No. | R | Compd. No. | R |
|---|---|---|---|
| 67 | [structure] | 74 | [structure] |
| 68 | [structure] | 75 | [structure] |
| 69 | [structure] | 76 | [structure] |
| 70 | [structure] | 77 | [structure] |
| 71 | [structure] | | |
| 72 | [structure] | | |
| 73 | [structure] | | |

*; (S) form, **; (R) form

The activity of Compound (I) as a smooth muscle relaxant which is useful as a therapeutic agent for urinary incontinence can be observed, for example, using the following tests. In the following Test Examples 1 and 2, "IC$_{50}$" means the concentration of a test compound which induces the decrease in the contraction of detrusor muscle by 50%.

TEST EXAMPLE 1

Male albino Hartley guinea pigs (350–550 g) were used as test animals. Each animal was exsanguinated to death under pentobarbital sodium anesthesia. The lower abdominal cavity was opened and its bladder was positioned. The connective tissue and the fat tissue around the bladder were removed, and the bladder was cleaned. After two pelvic nerves on the surface of the abdominal side of the bladder were dissected, the bladder was taken out on the entrance of ureter. The bladder was washed with a Krebs-Henseleit buffer [composition (mM): NaCl 118, KCl 4.7, MgSO$_4$ 1.2, KH$_2$PO$_4$ 1.2, CaCl$_2$ 2.5, NaHCO$_3$ 25, and D-glucose 11.1], and then put on a gauze patch soaked in the buffer in a Petri dish. The dome and the trigone of the bladder were dissected and discarded. The back of the bladder was cut vertically in the middle with scissors, and the bladder was put flat on the gauze patch. The dome tip and the side of the trigone of the bladder were dissected and discarded, and the mucosa of the bladder was removed. The back of the bladder was cut vertically to get 6 strips which are ca. 2.0 mm wide and ca. 10 mm long.

One end of each strip was fixed on a plastic supporter rod, and the other end was fixed on a clip connected to a suture thread. The supporter was fixed in 20 ml of an organ bath and the suture thread connected to the clip was fixed on a force-displacement transducer (NIHON KODEN TB-611T). The tissue was suspended in a Krebs-Henseleit buffer, and the bath solution was warmed to 37° C. and bubbled with a gas mixture of 5% $CO_2$ and 95% $O_2$. The pH of the solution was adjusted to about 7.4. The transducer was connected to a polygraph (NIHON KODEN AP-621G), and the change of tension was recorded on a recorder (YOKOGAWA type 3066). The polygraph was graduated by 0.5 g/cm.

After the tissue was incubated in the buffer for 15 minutes without preloading, tension was added thereto for about one hour. The preloading tension added was 1.5 g and it was relaxed to about 1 g. The tissue was washed at intervals of 15 minutes and the tension was adjusted to 1.5 g just before washing. The tension of the tissue was adjusted to be a steady state at 1 g. After this equilibrium time, 50 mM KCl (the whole content in the bath) was added, and the tissue was washed 10 minutes later. KCl was added to the tissue at intervals of 30 minutes, followed by washing 10 minutes later, and KCl was applied repeatedly until the developed tension induced by KCl becomes constant. When the tissue was confirmed to contract constantly by the application of KCl and relax to the steady state after washing, 50 mM KCl was applied again. After the tissue reached the steady state and the base line was obtained, a test compound was applied by the cumulative method (half-logarithmic incremence). The contact time at each concentration was 30 minutes. The activity of the compound was expressed as the maximum relaxation rate (%) of the tension induced by the agonist.

The results are shown in Table 2.

The effect of a smooth muscle relaxant varies with the concentration of KCl based on the difference of an action mechanism. In the following Test Example, KCl was used at a concentration different from that in Test Example 1.

TEST EXAMPLE 2

A sample of the excised bladder was prepared in the same manner as in Test Example 1, and the tension of the preparation was measured. After the tension of the tissue was adjusted to be a steady state at 1 g, 15 mM KCl was applied. After the rhythmical contraction was confirmed to appear by KCl, the tissue was washed. Then, 15 mM KCl was applied again. After the rhythmical contraction took place constantly and the tissue reached the steady state, a test compound was applied by the cumulative method (half-logarithmic incremence). The contact time at each concentration was 30 minutes. The activity of the compound was expressed as the maximum relaxation rate (%) of the tension induced by the agonist.

The results are shown in Table 2.

TABLE 2

| Compound No. | $IC_{50}$ (μM) KCl 50 mM | $IC_{50}$ (μM) KCl 15 mM |
|---|---|---|
| 1 | 1.7 | 2.4 |
| 2 | 3.6 | 3.4 |
| 3 | 2.2 | 1.8 |
| 4 | 2.6 | 8.4 |
| 5 | 8.0 | 2.1 |
| 6 | 6.1 | 11.2 |

TABLE 2-continued

| Compound No. | $IC_{50}$ (μM) KCl 50 mM | $IC_{50}$ (μM) KCl 15 mM |
|---|---|---|
| 7 | 2.4 | 2.1 |
| 8 | 5.2 | 0.5 |
| 9 | 4.3 | 4.6 |
| 10 | 10.0 | 1.9 |
| 11 | 2.0 | 2.2 |
| 12 | 3.8 | 3.2 |
| 13 | 3.5 | 48 |
| 14 | 5.7 | 2.3 |
| 15 | 7.1 | 9.4 |
| 16 | >10.0 | 1.4 |
| 18 | >10.0 | 2.1 |
| 20 | 2.3 | 6.0 |
| 21 | 4.3 | >10.0 |
| 22 | 4.2 | >10.0 |
| 23 | >10.0 | 7.8 |
| 25 | 2.2 | >10.0 |
| 26 | 7.1 | >10.0 |
| 27 | 4.8 | >10.0 |
| 33 | 1.1 | 2.7 |
| 34 | 1.6 | 2.2 |
| 35 | 31 | 1.0 |
| 36 | 8.3 | 1.3 |
| 37 | 4.3 | 0.2 |
| 38 | 13.4 | 0.9 |
| 39 | >10.0 | 2.6 |
| 40 | 1.5 | 3.5 |
| 41 | 2.1 | 1.6 |
| 42 | 4.7 | 1.5 |
| 43 | 3.5 | 2.1 |
| 45 | >10.0 | 2.5 |
| 47 | NT | 6.1 |
| 49 | 7.8 | 4.1 |
| 50 | NT | 6.1 |
| 51 | NT | 5.7 |
| 53 | >10.0 | 2.9 |
| 54 | 3.8 | >10.0 |
| 59 | >10.0 | 5.0 |
| 60 | >10.0 | 4.1 |
| 61 | 3.2 | 2.3 |
| 62 | 9.3 | >10.0 |
| 63 | 3.3 | >10.0 |
| 65 | 4.6 | 2.3 |
| 66 | 1.4 | 2.1 |
| 67 | 6.9 | 3.8 |
| 68 | >10.0 | 3.5 |

NT; not tested

The effect of the compounds of the present invention can also be proved by the standard examination method described below which is used to evaluate the smooth muscle relaxing activity.

TEST EXAMPLE 3

Female SD strain rats (120–180 g) were used as test animals. Each animal was anesthetized by subcutaneous administration of 1 g/kg urethane. A catheter was inserted into the trachea to secure respiration. A polyethylene cannula (PE50) was inserted into the bladder from the entrance of the urethra and the urethra was ligated at the base. A catheter for blood pressure measurement was inserted into the right carotid artery, and a cannula for drug administration was inserted into the right jugular vein. The arterial catheter and the vesical catheter were connected to pressure transducers to measure the blood pressure and the intravesical pressure. After the bladder was stabilized over about 15 minutes, physiological saline was injected into the bladder at a volume of 0.2–0.7 ml to induce the rhythmical contraction almost once a minute. After the contraction of the bladder started, the contraction pattern was stabilized for 30–45 minutes, followed by intravenous administration of a test compound.

By this examination method, the effect of the test compounds on both blood pressure and vesical contraction can be evaluated. The blood pressure was measured 5, 15, and 30 minutes after the test compound was injected into the vein. Micturition contraction was induced by injecting physiological saline into the bladder. The change of average contraction interval (time between contractions) over 20 minutes was expressed as the relative value based on the pre-administration value which was regarded as 100.

The results are shown in Table 3.

TABLE 3

| Compound No. | Dose (mg/kg) | Change of average arterial blood pressure (%) | | | Change of contraction interval (%) |
|---|---|---|---|---|---|
| | | 5 min. | 15 min. | 30 min. | |
| 1 | 1 | +5 | +5 | +5 | +150 |
| 7 | 1 | −4 | +1 | +4 | +186 |

The following is a test which is useful to prove that a test compound shows the selectivity to the bladder without exhibiting cardiovascular activity when orally administered.

TEST EXAMPLE 4

Male SD strain rats (200–300 g) were used as test animals. Each animal was anesthetized by intraperitoneal administration of 50 mg/kg Nembutal. The hair on the abdomen, the thigh, and the back of the neck was shaved, followed by disinfection with 70% ethanol. The left femoral artery of the rat was exposed by incising the thigh for the insertion of a catheter into the femoral artery. A catheter filled with physiological saline containing heparin (1000 units/ml) was introduced into the artery by 2–3 cm to position the tip of the catheter in the abdominal artery. The end of the catheter was exposed outside the body from the back of the neck, stoppered, and fixed on the skin tightly. A catheter for the bladder was inserted according to the method of Yaksh, T. L., Durant, P. A. C. and Brent, C. R. [(Micturition in rats: A chronic model for study of bladder function and effect of anesthesia. Am. J. Physiol., 251, R1177–1185 (1986)]. The bladder was exposed by middle incision. The bladder dome was given a small incision to make a small hole. A catheter filled with physiological saline was inserted into the bladder and was fixed thereto by ligation with a silk thread. The other end of the catheter was exposed outside the body from the back of the neck of the rat after being passed under the skin using a trocar. The exposed end of the catheter was stoppered and fixed on the skin tightly. The abdominal muscles and skin were sutured, and the test animal was recovered from anesthesia.

The rat was weighed 24–48 hours after the operation, put in a Bollman cage (NATSUME SEISAKUSHO), and subjected to the test under partial restraint. The arterial catheter was connected to a pressure transducer (NIHON KODEN DX-300) used for the measurement of blood pressure. The vesical catheter was connected to a pump for injecting physiological saline and a pressure transducer with PE50 and a three-way stop-cock. Injection of physiological saline (0.15 ml/minute) through the bladder was started and continued during the test. The changes of blood pressure, heart rate, and intravesical pressure were recorded with a polygraph (NIHON KODEN). The test animal was equilibrated (ca. 60–120 minutes) until its micturition pattern was constant. At this point, the basal value of each test parameter was recorded, and the rat was compulsorily given a test compound (in 0.3% carboxymethyl cellulose-physiological saline) at a volume of 1 ml/kg (body weight) by oral administration. The effects of the compound on the test parameters were observed for 5 hours after the administration. As a control compound, cromakalim was used. The contraction interval, the systemic blood pressure, and the heart rate were measured for 5 hours after the administration of the compound at one-hour intervals and were expressed as the relative values based on the pre-administration values which were regarded as 100.

The results are shown in Tables 4 and 5. As for the compounds other than Compounds 1 and 7, the results are shown only in respect of the change of the contraction interval.

TABLE 4

| Compound | Time (hr) | Contraction interval | Blood pressure | Heart rate |
|---|---|---|---|---|
| Solvent alone 1 ml/kg | 0 | 100 | 100 | 100 |
| | 1 | 79 | 101 | 98 |
| | 2 | 100 | 101 | 100 |
| | 3 | 110 | 103 | 98 |
| | 4 | 104 | 100 | 99 |
| | 5 | 107 | 100 | 100 |
| Cromakalim 1 mg/kg | 0 | 100 | 100 | 100 |
| | 1 | 128 | 46 | 98 |
| | 2 | 133 | 51 | 93 |
| | 3 | 142 | 54 | 96 |
| | 4 | 133 | 60 | 97 |
| | 5 | 133 | 64 | 102 |
| Compound 1 3 mg/kg | 0 | 100 | 100 | 100 |
| | 1 | 136 | 98 | 98 |
| | 2 | 148 | 99 | 98 |
| | 3 | 134 | 96 | 96 |
| | 4 | 122 | 91 | 93 |
| | 5 | 117 | 91 | 89 |
| Compound 7 3 mg/kg | 0 | 100 | 100 | 100 |
| | 1 | 132 | 100 | 103 |
| | 2 | 141 | 96 | 103 |
| | 3 | 149 | 99 | 103 |
| | 4 | 154 | 101 | 106 |
| | 5 | 146 | 101 | 105 |

| Compound | Dose (mg/kg) | Time after administration (hr) | Contraction interval |
|---|---|---|---|
| Compound 9 | 1.0 | 1 | 123.4 ± 6.8 |
| | | 2 | 131.2 ± 9.3 |
| | | 3 | 132.9 ± 9.1 |
| | | 4 | 145.0 ± 10.0 |
| | | 5 | 154.9 ± 12.2 |
| Compound 10 | 1.0 | 1 | 132.4 ± 11.2 |
| | | 2 | 142.0 ± 17.5 |
| | | 3 | 158.4 ± 22.3 |
| | | 4 | 173.8 ± 29.9 |
| | | 5 | 182.7 ± 42.7 |
| Compound 8 | 1.0 | 1 | 130.3 ± 9.3 |
| | | 2 | 142.1 ± 12.6 |
| | | 3 | 144.3 ± 8.8 |
| | | 4 | 162.4 ± 14.6 |
| | | 5 | 189.4 ± 19.6 |
| Compound 33 | 0.1 | 1 | 135.1 ± 21.7 |
| | | 2 | 145.6 ± 25.5 |
| | | 3 | 143.4 ± 24.4 |
| | | 4 | 156.3 ± 30.6 |
| | | 5 | 160.6 ± 37.4 |
| Compound 37 | 1.0 | 1 | 113.5 ± 10.7 |
| | | 2 | 127.9 ± 6.5 |
| | | 3 | 126.5 ± 6.5 |
| | | 4 | 140.4 ± 10.2 |
| | | 5 | 143.6 ± 11.1 |
| Compound 35 | 1.0 | 1 | 123.2 ± 8.8 |
| | | 2 | 123.8 ± 5.7 |
| | | 3 | 130.7 ± 9.8 |
| | | 4 | 137.9 ± 11.0 |

TABLE 4-continued

| | | | |
|---|---|---|---|
| | | 5 | 143.6 ± 8.9 |
| Compound 2 | 1.0 | 1 | 120.9 ± 6.2 |
| | | 2 | 135.4 ± 12.3 |
| | | 3 | 144.5 ± 16.3 |
| | | 4 | 140.8 ± 15.6 |
| | | 5 | 144.9 ± 16.0 |
| Compound 5 | 1.0 | 1 | 111.6 ± 7.0 |
| | | 2 | 135.5 ± 16.5 |
| | | 3 | 137.4 ± 14.5 |
| | | 4 | 131.5 ± 9.5 |
| | | 5 | 130.8 ± 17.7 |
| Compound 15 | 1.0 | 1 | 129.9 ± 9.5 |
| | | 2 | 127.8 ± 5.3 |
| | | 3 | 107.3 ± 16.5 |
| | | 4 | 120.7 ± 11.4 |
| | | 5 | 134.6 ± 12.6 |
| Compound 16 | 1.0 | 1 | 118.0 ± 7.9 |
| | | 2 | 132.3 ± 14.2 |
| | | 3 | 119.2 ± 9.8 |
| | | 4 | 126.9 ± 7.1 |
| | | 5 | 136.8 ± 12.6 |
| Compound 20 | 1.0 | 1 | 121.2 ± 3.9 |
| | | 2 | 146.6 ± 9.9 |
| | | 3 | 148.4 ± 20.0 |
| | | 4 | 155.8 ± 19.6 |
| | | 5 | 142.2 ± 15.8 |
| Compound 53 | 1.0 | 1 | 108.4 ± 9.7 |
| | | 2 | 134.5 ± 12.0 |
| | | 3 | 148.4 ± 14.0 |
| | | 4 | 155.3 ± 11.9 |
| | | 5 | 167.9 ± 11.8 |

Compound (I) can be formulated into generally employed dose forms such as tablets, capsules and syrups, and administered orally or parenterally through intramuscular injection, intravenous injection, drip infusion, or rectal administration in the form of suppositories. For preparing these dose forms for oral or parenteral administration, generally known methods are applied. For example, the preparations may be formulated to contain various excipients, lubricants, binders, disintegrating agents, isotonizing agents, emulsifiers, and the like.

Examples of the carriers which can be used are water, injectable distilled water, physiological saline, glucose, fructose, sucrose, mannitol, lactose, starch, cellulose, methyl cellulose, sulfoxymethyl cellulose, hydroxypropyl cellulose, alginic acid, talc, sodium citrate, calcium carbonate, calcium hydrogenphosphate, magnesium stearate, urea, silicone resins, sorbitan fatty acid esters, and glycerin fatty acid esters.

The effective dose and the administration schedule of Compound (I) vary depending upon the mode of administration, the age and body weight of a patient, and the type or degree of the disease to be treated, but generally, in the case of oral administration, Compound (I) is administered in a dose of 0.01 mg to 1 g/adult/day, preferably 0.05 to 50 mg/adult/day, in one to several parts. In the case of parenteral administration such as intravenous injection, Compound (I) is administered in a dose of 0.001 to 100 mg/adult/day, preferably 0.01 to 10 mg/adult/day, in one to several parts. It should, however, be noted that the dose may vary depending upon various conditions as given above.

Certain embodiments of the present invention are illustrated in the following Examples and Reference Examples.

BEST MODE FOR CARRYING OUT THE INVENTION

EXAMPLE 1

1-(3,3,3-Trifluoro-2-hydroxy-2-methylpropanoylamino)-6,11-dihydrodibenz[b,e]oxepin-11-one (Compound 1)

In dimethylacetamide (3 ml) was dissolved 3,3,3-trifluoro-2-hydroxy-2-methylpropionic acid (0.17 g, 1.1 mmol), and thionyl chloride (80 µl, 1.1 mmol) was added thereto at $-15°$ C., followed by stirring at $-15$ to $-5°$ C. for one hour. To this reaction mixture was added 1-amino-6,11-dihydrodibenz[b,e]oxepin-11-one obtained in Reference Example 4 (0.17 g, 0.77 mmol), and the mixture was stirred overnight at room temperature. After concentration of the reaction mixture under reduced pressure, the obtained oily residue was dissolved in ethyl acetate (20 ml). The organic layer was washed successively with a 5% aqueous solution of sodium bicarbonate and a saturated aqueous solution of sodium chloride, and then dried over anhydrous magnesium sulfate. After the drying agent was filtered off, the organic layer was concentrated under reduced pressure. The obtained oily residue was purified by silica gel column chromatography (hexane/ethyl acetate=5/1), followed by trituration with hexane to give Compound 1 (80 mg, 30%).

$^1$H-NMR (CDCl$_3$) δ:1.61(s, 3H), 4.47(br, 1H), 5.18(s, 2H), 6.89(d, 1H, J=7.9 Hz), 7.34(d, 1H, J=7.9 Hz), 7.45–7.54(m, 3H), 7.86(d, 1H, J=7.9 Hz), 8.42(d, 1H, J=7.9 Hz), 12.88(br, 1H)

In the following Examples 2 to 6, substantially the same procedure as in Example 1 was repeated except that the corresponding tricyclic aromatic amine was used instead of 1-amino-6,11-dihydrodibenz[b,e]oxepin-11-one, to give the desired compound.

EXAMPLE 2

3-(3,3,3-Trifluoro-2-hydroxy-2-methylpropanoylamino)-6,11-dihydrodibenz[b,e]oxepin-11-one (Compound 2) (yield:45%)

$^1$H-NMR (CDCl$_3$) δ:1.62(s, 3H), 3.69(br, 1H), 5.20(s, 2H), 7.19(d, 1H, J=8.1 Hz), 7.37(d, 1H, J=8.1 Hz), 7.45–7.60(m, 3H), 7.92(d, 1H, J=8.1 Hz), 8.25(d, 1H, J=8.1 Hz), 8.52(br, 1H)

EXAMPLE 3

2-(3,3,3-Trifluoro-2-hydroxy-2-methylpropanoylamino)-6,11-dihydrodibenz[b,e]oxepin-11-one (Compound 3) (yield:45%)

$^1$H-NMR (DMSO-d$_6$) δ:1.59(s, 3H), 5.27(s, 2H), 7.06(d, 1H, J=7.9 Hz), 7.36(s, 1H), 7.50–7.56(m, 2H), 7.63–7.68(m, 1H), 7.79(d, 1H, J=7.9 Hz), 7.86(s, 1H), 10.10(br, 1H)

EXAMPLE 4

1-(3,3,3-Trifluoro-2-hydroxy-2-methylpropanoylamino)fluoren-9-one (Compound 4) (yield:48%)

$^1$H-NMR (DMSO-d$_6$) δ:1.62(s, 3H), 7.39(t, 1H, J=7.5 Hz), 7.50(d, 1H, J=7.5 Hz), 7.57–7.63(m, 3H), 7.78(d, 1H, J=7.5 Hz), 7.92(s, 1H), 8.32(d, 1H, J=7.5 Hz), 11.36(br, 1H)

EXAMPLE 5

2-(3,3,3-Trifluoro-2-hydroxy-2-methylpropanoylamino)fluoren-9-one (Compound 5) (yield:90%)

$^1$H-NMR (DMSO-d$_6$) δ:1.62(s, 3H), 7.31(t, 1H, J=7.8 Hz), 7.41(br, 1H), 7.53(d, 2H, J=7.8 Hz), 7.67(d, 2H, J=7.8 Hz), 7.93(d, 1H, j=7.8 Hz), 8.09(s, 1H), 10.17(br, 1H)

EXAMPLE 6

3-(3,3,3-Trifluoro-2-hydroxy-2-methylpropanoylamino)fluoren-9-one (Compound 6) (yield:67%)

$^1$H-NMR (DMSO-d$_6$) δ:1.64(s, 3H), 7.36(d, 1H, J=7.1 Hz), 7.48–7.58(m, 3H), 7.62(d, 1H, J=7.1 Hz), 7.74(d, 1H, J=7.1 Hz), 8.21(s, 1H), 10.21(br, 1H)

EXAMPLE 7

9-(3,3,3-Trifluoro-2-hydroxy-2-methylpropanoylamino)-4,10-dihydrothieno[3,2-c][1]benzoxepin-10-one (Compound 7)

In dimethylacetamide (3 ml) was dissolved 3,3,3-trifluoro-2-hydroxy-2-methylpropionic acid (0.32 g, 2.03 mmol), and thionyl chloride (148 μl, 2.03 mmol) was added thereto at −15° C., followed by stirring at −15° to −5° C. for one hour. To this reaction mixture was added 9-amino-4,10-dihydrothieno[3,2-c][1]benzoxepin-10-one obtained in Reference Example 11 (0.23 g, 1.02 mmol), and the mixture was stirred overnight at room temperature. After concentration of the reaction mixture under reduced pressure, the obtained oily residue was dissolved in ethyl acetate (20 ml). The organic layer was washed successively with a 5% aqueous solution of sodium bicarbonate and a saturated aqueous solution of sodium chloride, and then dried over anhydrous magnesium sulfate. After the drying agent was filtered off, the organic layer was concentrated under reduced pressure. The obtained oily residue was purified by silica gel column chromatography (hexane/ethyl acetate=5/1), followed by trituration with hexane to give Compound 7 (0.34 g, 89%).

$^1$H-NMR (CDCl$_3$) δ:1.77(s, 3H), 4.32(s, 1H), 5.16(s, 2H), 7.00–7.04(m, 2H), 7.54(t, 1H, J=8.4 Hz), 7.72(d, 1H, J=5.0 Hz), 8.41(d, 1H, J=8.4 Hz), 12.24(br, 1H)

In the following Examples 8 to 32, 35 to 51, and 69 to 77, substantially the same procedure as in Example 7 was repeated except that the corresponding tricyclic aromatic amine was used instead of 9-amino-4,10-dihydorothieno[3,2-c][1]benzoxepin-10-one, to give the desired compound.

EXAMPLE 8

7-(3,3,3-Trifluoro-2-hydroxy-2-methylpropanoylamino)-4,10-dihydrothieno[3,2-c][1]benzoxepin-10-one (Compound 8) (yield:64%)

$^1$H-NMR (DMSO-d$_6$) δ:1.60(s, 3H), 5.29(s, 2H), 7.22(d, 1H, J=5.0 Hz), 7.52(s, 1H), 7.68(d, 1H, J=8.6 Hz), 7.75(s, 1H), 7.98–8.00(m, 2H), 10.31(br, 1H)

EXAMPLE 9

5-(3,3,3-Trifluoro-2-hydroxy-2-methylpropanoylamino)-4,10-dihydrofuro[2,3-c][1]benzoxepin-4-one (Compound 9) (yield:67%)

$^1$H-NMR (CDCl$_3$) δ:1.77(s, 3H), 4.28(s, 1H), 5.17(s, 2H), 6.96(d, 1H, J=2.0 Hz), 7.03(d, 1H, J=8.3 Hz), 7.39(d, 1H, J=2.0 Hz), 7.48(t, 1H, J=8.3 Hz), 8.42 (d, 1H, J=8.3 Hz), 12.13(br, 1H)

EXAMPLE 10

7-(3,3,3-Trifluoro-2-hydroxy-2-methylpropanoylamino)-4,10-dihydrofuro[2,3-c][1]benzoxepin-4-one (Compound 10) (yield:75%)

$^1$H-NMR (DMSO-d$_6$) δ:1.62(s, 3H), 5.28(s, 2H), 6.90(d, 1H, J=2.0 Hz), 7.40(s, 1H), 7.62–7.69(m, 2H), 7.76 (s, 1H), 7.96(d, 1H, J=8.9 Hz), 10.13(br, 1H)

EXAMPLE 11

3-Chloro-2-(3,3,3-trifluoro-2-hydroxy-2-methylpropanoylamino)fluoren-9-one (Compound 11) (yield: 59%)

$^1$H-NMR (DMSO-d$_6$) δ:1.63(s, 3H), 7.39(t, 1H, J=7.7 Hz), 7.59–7.65(m, 2H), 7.82(d, 1H, J=7.7 Hz), 8.07(s, 1H), 8.26(d, 1H, J=7.7 Hz)

EXAMPLE 12

3-Bromo-2-(3,3,3-trifluoro-2-hydroxy-2-methylpropanoylamino)fluoren-9-one (Compound 12) (yield: 90%)

$^1$H-NMR (DMSO-d$_6$) δ:1.64(s, 3H), 7.38(t, 1H, J=7.3 Hz), 7.59–7.65(m, 2H), 7.82(d, 1H, J=7.3 Hz), 8.22(s, 1H), 8.26(s, 1H), 9.83(br, 1H)

EXAMPLE 13

7-Bromo-2-(3,3,3-trifluoro-2-hydroxy-2-methylpropanoylamino)fluoren-9-one (Compound 13) (yield: 98%)

$^1$H-NMR (DMSO-d$_6$) δ:1.59(s, 3H), 7.43(br, 1H), 7.66–7.77(m, 4H), 7.96(d, 1H, J=8.2 Hz), 8.10(s, 1H), 10.23(br, 1H)

EXAMPLE 14

4-(3,3,3-Trifluoro-2-hydroxy-2-methylpropanoylamino)fluoren-9-one (Compound 14) (yield:75%)

$^1$H-NMR (DMSO-d$_6$) δ:1.67(s, 3H), 7.36–7.42(m, 2H), 7.52–7.68(m, 5H), 10.24(br, 1H)

EXAMPLE 15

9-(3,3,3-Trifluoro-2-hydroxy-2-methylpropanoylamino)-4,10-dihydrofuro[3,2-c][1]benzoxepin-10-one (Compound 15) (yield:84%)

$^1$H-NMR (CDCl$_3$) δ:1.60(s, 3H), 4.32(br, 1H), 5.11(s, 2H), 6.53(d, 1H, J=2.0 Hz), 7.03(d, 1H, J=8.3 Hz), 7.54(t, 1H, J=8.3 Hz), 7.71(d, 1H, J=2.0 Hz), 8.46 (d, 1H, J=8.3 Hz), 12.35(br, 1H)

EXAMPLE 16

8-(3,3,3-Trifluoro-2-hydroxy-2-methylpropanoylamino)-4,10-dihydrothieno[3,2-c][1]benzoxepin-10-one (Compound 16) (yield:55%)

$^1$H-NMR (CDCl$_3$) δ:1.60(s, 3H), 5.26(s, 2H), 7.15(d, 1H, J=8.9 Hz), 7.21(d, 1H, J=5.0 Hz), 7.35(br, 1H), 7.93(d, 1H, J=8.9 Hz), 7.98(d, 1H, J=5.0 Hz), 8.42 (s, 1H), 10.14(br, 1H)

EXAMPLE 17

5-(3,3,3-Trifluoro-2-hydroxy-2-methylpropanoylamino)-4,10-dihydrothieno[2,3-c][1]benzoxepin-4-one (Compound 17) (yield:65%)

$^1$H-NMR (CDCl$_3$) δ:1.78(s, 3H), 4.33(s, 1H), 5.29(s, 2H), 7.01(dd, 1H, J=8.3, 1.3 Hz), 7.20(d, 1H, J=5.3 Hz), 7.53(t, 1H, J=8.9 Hz), 7.72(d, 1H, J=5.3 Hz), 8.39(dd, 1H, J=8.3, 1.3 Hz), 12.30(br, 1H)

EXAMPLE 18

7-(3,3,3-Trifluoro-2-hydroxy-2-methylpropanoylamino)-4,10-dihydrothieno[2,3-c][1]benzoxepin-4-one (Compound 18) (yield:27%)

$^1$H-NMR (DMSO-d$_6$) δ:1.59(s, 3H), 5.43(s, 2H), 7.54(s, 2H), 7.59(br, 1H), 7.69(m, 2H), 8.09(d, 1H, J=8.6 Hz), 10.37(br, 1H)

EXAMPLE 19

6-Bromo-9-(3,3,3-trifluoro-2-hydroxy-2-methylpropanoylamino)-4,10-dihydrothieno[3,2-c][1]-benzoxepin-10-one (Compound 19) (yield:36%)

$^1$H-NMR (CDCl$_3$) δ:1.76(s, 3H), 4.19(br, 1H), 5.24(s, 2H), 7.01(d, 1H, J=5.3 Hz), 7.75(d, 1H, J=5.3 Hz), 7.78(d, 1H, J=9.1 Hz), 8.34(d, 1H, J=9.1 Hz), 11.94 (br, 1H)

EXAMPLE 20

7-Fluoro-1-(3,3,3-trifluoro-2-hydroxy-2-methylpropanoylamino)-6,11-dihydrodibenz[b,e]oxepin-11-one (Compound 20) (yield:87%)

$^1$H-NMR (CDCl$_3$) δ:1.81(s, 3H), 4.37(br, 1H), 5.30(s, 2H), 6.92(d, 1H, J=8.3 Hz), 7.31(t, 1H, J=8.3 Hz), 7.34–7.48 (m, 1H), 7.53(t, 1H, J=8.3 Hz), 7.66(d, 1H, J=8.3 Hz), 8.40(d, 1H, J=8.3 Hz), 12.52(br, 1H)

EXAMPLE 21

7-Fluoro-3-(3,3,3-trifluoro-2-hydroxy-2-methylpropanoylamino)-6,11-dihydrodibenz[b,e]oxepin-11-one (Compound 21) (yield:96%)

$^1$H-NMR (CDCl$_3$) δ:1.76(s, 3H), 3.83(br, 1H), 5.32(s, 2H), 7.22(d, 1H, J=8.6 Hz), 7.26–7.34(m, 1H), 7.39–7.47(m, 1H), 7.51(s, 1H), 7.67(d, 1H, J=8.6 Hz), 8.21(d, 1H, J=8.6 Hz), 8.58(br, 1H)

EXAMPLE 22

3-Methyl-1-(3,3,3-trifluoro-2-hydroxy-2-methylpropanoylamino)-6,11-dihydrodibenz[b,e]oxepin-11-one (Compound 22) (yield:92%)

$^1$H-NMR (CDCl$_3$) δ:1.81(s, 3H), 2.24(s, 3H), 4.46(br, 1H), 5.21(s, 2H), 7.34(d, 1H, J=7.4 Hz), 7.39(d, 1H, J=8.6 Hz), 7.45(t, 1H, J=7.4 Hz), 7.58(t, 1H, J=7.4 Hz), 7.87(d, 1H, J=7.4 Hz), 8.26(d, 1H, J=8.6 Hz), 12.57(br, 1H)

EXAMPLE 23

3-Methoxy-1-(3,3,3-trifluoro-2-hydroxy-2-methylpropanoylamino)-6,11-dihydrodibenz[b,e]oxepin-11-one (Compound 23) (yield:30%)

$^1$H-NMR (CDCl$_3$) δ:1.80(s, 3H), 3.91(s, 3H), 4.50(br, 1H), 5.28(s, 2H), 7.13(d, 1H, J=9.2 Hz), 7.32(t, 1H, J=7.6 Hz), 7.47(t, 1H, J=7.6 Hz), 7.57(t, 1H, J=7.6 Hz), 7.85(d, 1H, J=7.6 Hz), 8.31(d, 1H, J=9.2 Hz), 12.52 (br, 1H)

EXAMPLE 24

2-Methyl-1-(3,3,3-trifluoro-2-hydroxy-2-methylpropanoylamino)-6,11-dihydrodibenz[b,e]oxepin-11-one (Compound 24) (yield:10%)

$^1$H-NMR (CDCl$_3$) δ:1.76(s, 3H), 2.19(s, 3H), 4.28(br, 1H), 5.24(s, 2H), 7.01(d, 1H, J=8.3 Hz), 7.25(d, 1H, J=7.3 Hz), 7.35(d, 1H, J=8.3 Hz), 7.44(t, 1H, J=7.6 Hz), 7.55(t, 1H, J=7.6 Hz), 7.95(d, 1H, J=7.6 Hz), 9.84(br, 1H)

EXAMPLE 25

2-Methyl-3-(3,3,3-trifluoro-2-hydroxy-2-methylpropanoylamino)-6,11-dihydrodibenz[b,e]oxepin-11-one (Compound 25) (yield:14%)

$^1$H-NMR (DMSO-d$_6$) δ:1.76(s, 3H), 2.28(s, 3H), 3.92(br, 1H), 5.17(s, 2H), 7.36(d, 1H, J=7.5 Hz), 7.47(t, 1H, J=7.5 Hz), 7.56(t, 1H, J=7.5 Hz), 7.91(d, 1H, J=7.5 Hz), 7.97(s, 1H), 8.09(s, 1H), 8.54(br, 1H)

EXAMPLE 26

6-Methyl-9-(3,3,3-trifluoro-2-hydroxy-2-methylpropanoylamino)-4,10-dihydrothieno[3,2-c][1]-benzoxepin-10-one (Compound 26) (yield:90%)

$^1$H-NMR (CDCl$_3$) δ:1.75(s, 3H), 2.32(s, 3H), 4.34(br, 1H), 5.17(s, 2H), 6.99(d, 1H, J=5.1 Hz), 7.42(d, 1H, J=8.4 Hz), 7.70(d, 1H, J=5.1 Hz), 8.25(d, 1H, J=8.4 Hz), 11.92(br, 1H)

EXAMPLE 27

6-Methoxy-9-(3,3,3-trifluoro-2-hydroxy-2-methylpropanoylamino)-4,10-dihydrothieno[3,2-c][1]-benzoxepin-10-one (Compound 27) (yield:95%)

$^1$H-NMR (CDCl$_3$) δ:1.75(s, 3H), 3.91(s, 3H), 5.19(s, 2H), 6.97(d, 1H, J=5.0 Hz), 7.15(d, 1H, J=9.2 Hz), 7.69(d, 1H, J=5.0 Hz), 8.27(d, 1H, J=9.2 Hz), 11.62(br, 1H)

EXAMPLE 28

8-Methyl-5-(3,3,3-trifluoro-2-hydroxy-2-methylpropanoylamino)-4,10-dihydrofuro[2,3-c][1]benzoxepin-4-one (Compound 28) (yield:87%)

$^1$H-NMR (CDCl$_3$) δ:1.75(s, 3H), 2.33(s, 3H), 4.34(br, 1H), 5.13(s, 2H), 6.94(d, 1H, J=2.0 Hz), 7.39(d, 1H, J=2.0 Hz), 7.41(d, 1H, J=8.6 Hz), 8.27(d, 1H, J=8.6 Hz), 11.81(br, 1H)

EXAMPLE 29

8-Methoxy-5-(3,3,3-trifluoro-2-hydroxy-2-methylpropanoylamino)-4,10-dihydrofuro[2,3-c][1]benzoxepin-4-one (Compound 29) (yield:89%)

$^1$H-NMR (CDCl$_3$) δ:1.74(s, 3H), 3.93(s, 3H), 4.37(br, 1H), 5.17(s, 2H), 6.93(d, 1H, J=2.0 Hz), 7.15(d, 1H, J=9.2 Hz), 7.39(d, 1H, J=2.0 Hz), 8.30(d, 1H, J=9.2 Hz), 11.49(br, 1H)

EXAMPLE 30

7-(3,3,3-Trifluoro-2-hydroxy-2-methylpropanoylamino)-5,11-dihydropyrido[2,3-c][1]benzoxepin-5-one (Compound 30(yield:47%)

$^1$H-NMR (DMSO-d$_6$) δ:1.65(s, 3H), 5.44(s, 2H), 7.22(d, 1H, J=8.9 Hz), 7.50(br, 1H), 7.68(dd, 1H, J=7.9, 5.0 Hz), 7.97(dd, 1H, J=8.9, 3.0 Hz), 8.32(dd, 1H, J=7.9, 2.0 Hz), 8.63(d, 1H, J=3.0 Hz), 8.85(dd, 1H, J=5.0, 2.0 Hz), 10.28(br, 1H)

EXAMPLE 31

7-Methoxy-6-(3,3,3-trifluoro-2-hydroxy-2-methylpropanoylamino)-5,11-dihydropyrido[2,3-c][1]-benzoxepin-5-one (Compound 31) (yield:87%)

$^1$H-NMR (CDCl$_3$) δ:1.70(s, 3H), 3.90(s, 3H), 4.05(br, 1H), 5.41(s, 2H), 7.04(d, 1H, J=8.9 Hz), 7.12(d, 1H, J=8.9 Hz), 7.44(dd, 1H, J=7.9, 4.8 Hz), 8.31 (dd, 1H, J=7.9, 1.6 Hz), 8.69(dd, 1H, J=4.8, 1.6 Hz), 8.75(br, 1H)

EXAMPLE 32

7-Methyl-6-(3,3,3-trifluoro-2-hydroxy-2-methylpropanoylamino)-5,11-dihydropyrido[2,3-c][1]-benzoxepin-5-one (Compound 32) (yield:79%)

$^1$H-NMR (CDCl$_3$) δ:1.72(s, 3H), 2.23(s, 3H), 4.18(br, 1H), 5.38(s, 2H), 7.12(d, 1H, J=8.2 Hz), 7.36–7.44(m, 2H), 8.33(dd, 1H, J=8.3, 1.7 Hz), 8.70(dd, 1H, J=4.6, 1.7 Hz), 9.30(br, 1H)

EXAMPLE 33

(S)-9-(3,3,3-trifluoro-2-hydroxy-2-methylpropanoylamino)-4,10-dihydrothieno[3,2-c][1]benzoxepin-10-one (Compound 33)

Substantially the same procedure as in Example 1 was repeated using 9-amino-4,10-dihydrothieno[3,2-c][1]

benzoxepin-10-one obtained in Reference Example 11 (0.840 g, 3.63 mmol) and (S)-3,3,3-trifluoro-2-hydroxy-2-methylpropionic acid obtained in Reference Example 27 (1.14 g, 7.26 mmol) to give Compound 33 (0.47 g, 35%).

$^1$H-NMR (CDCl$_3$) δ:1.77(s, 3H), 4.28(br, 1H), 5.19(s, 2H), 7.00–7.04(m, 2H), 7.54(t, 1H, J=8.4 Hz), 7.72(d, 1H, J=5.0 Hz), 8.41(d, 1H, J=8.4 Hz), 12.24(br, 1H)

EXAMPLE 34

(R)-9-(3,3,3-Trifluoro-2-hydroxy-2-methylpropanoylamino)-4,10-dihydrothieno[3,2-c][1]benzoxepin-10-one (Compound 34) (yield:46%)

Substantially the same procedure as in Example 1 was repeated using 9-amino-4,10-dihydrothieno[3,2-c][1]benzoxepin-10-one obtained in Reference Example 11 (0.951 g, 4.11 mmol) and (R)-3,3,3-trifluoro-2-hydroxy-2-methylpropionic acid obtained in Reference Example 28 (1.17 g, 7.40 mmol) to give Compound 34 (0.70 g, 46%).

$^1$H-NMR (CDCl$_3$) δ:1.77(s, 3H), 4.28(br, 1H), 5.19(s, 2H), 7.00–7.04(m, 2H), 7.54(t, 1H, J=8.4 Hz), 7.72(d, 1H, J=5.0 Hz), 8.41(d, 1H, J=8.4 Hz), 12.24(br, 1H)

EXAMPLE 35

(S)-5-(3,3,3-Trifluoro-2-hydroxy-2-methylpropanoylamino)-4,10-dihydrofuro[2,3-c][1]benzoxepin-4-one (Compound 35) (yield:85%)

$^1$H-NMR (CDCl$_3$) δ:1.56(s, 3H), 4.27(br, 1H), 5.17(s, 2H), 6.97(d, 1H, J=2.0 Hz), 7.03(d, 1H, J=8.3 Hz), 7.39(d, 1H, J=2.0 Hz), 7.51(t, 1H, J=8.3 Hz), 8.42 (d, 1H, J=8.3 Hz), 12.13(br, 1H)

EXAMPLE 36

(R)-5-(3,3,3-Trifluoro-2-hydroxy-2-methylpropanoylamino)-4,10-dihydrofuro[2,3-c][1]benzoxepin-4-one (Compound 36) (yield:74%)

$^1$H-NMR (CDCl$_3$) δ:1.57(s, 3H), 4.29(br, 1H), 5.17(s, 2H), 6.96(d, 1H, J=2.0 Hz), 7.04(d, 1H, J=8.3 Hz), 7.39(d, 1H, J=2.0 Hz), 7.52(t, 1H, J=8.3 Hz), 8.42 (d, 1H, J=8.3 Hz), 12.12(br, 1H)

EXAMPLE 37

(S)-7-(3,3,3-Trifluoro-2-hydroxy-2-methylpropanoylamino)-4,10-dihydrofuro[2,3-c][1]benzoxepin-4-one (Compound 37) (yield:87%)

$^1$H-NMR (DMSO-d$_6$) δ:1.60(s, 3H), 5.31(s, 2H), 6.91(d, 1H, J=2.0 Hz), 7.50(br, 1H), 7.70–7.77(m, 3H), 7.95(d, 1H, J=8.9 Hz), 10.28(br, 1H)

EXAMPLE 38

(R)-7-(3,3,3-Trifluoro-2-hydroxy-2-methylpropanoylamino)-4,10-dihydrofuro[2,3-c][1]benzoxepin-4-one (Compound 38) (yield:56%)

$^1$H-NMR (DMSO-d$_6$) δ:1.60(s, 3H), 5.32(s, 1H), 6.92(d, 1H, J=2.0 Hz), 7.58(br, 1H), 7.69–7.76(m, 3H), 7.95(d, 1H, J=8.6 Hz), 10.30(br, 1H)

EXAMPLE 39

(S)-8-(3,3,3-Trifluoro-2-hydroxy-2-methylpropanoylamino)-4,10-dihydrothieno[3,2-c][1]benzoxepin-10-one (Compound 39) (yield:82%)

$^1$H-NMR (DMSO-d$_6$) δ:1.59(s, 3H), 5.26(s, 2H), 7.17(d, 1H, J=8.6 Hz), 7.24(d, 1H, J=5.0 Hz), 7.41(br, 1H), 7.92(d, 1H, J=8.6 Hz), 8.04(d, 1H, J=5.0 Hz), 8.42 (s, 1H), 10.19(br, 1H)

EXAMPLE 40

1-(3,3,3-Trifluoro-2-hydroxy-2-methylpropanoylamino)-6,11-dihydrodibenzo[b,e]thiepin-11-one (Compound 40) (yield:62%)

$^1$H-NMR (DMSO-d$_6$) δ:1.56(s, 3H), 4.26(s, 2H), 7.30(d, 1H, J=7.9 Hz), 7.36(t, 1H, J=7.9 Hz), 7.40–7.59(m, 3H), 7.56(d, 1H, J=7.9 Hz), 7.66(br, 1H), 7.94(d, 1H, J=7.9 Hz), 8.31(d, 1H, J=9.2 Hz), 10.73(br, 1H)

EXAMPLE 41

3-(3,3,3-Trifluoro-2-hydroxy-2-methylpropanoylamino)-6,11-dihydrodibenzo[b,e]thiepin-11-one (Compound 41) (yield:60%)

$^1$H-NMR (DMSO-d$_6$) δ:1.58(s, 3H), 4.22(s, 2H), 7.36–7.40(m, 2H), 7.48–7.52(m, 2H), 7.72(d, 1H, J=8.9 Hz), 7.94(s, 1H), 8.11(d, 1H, J=8.9 Hz), 8.31(d, 1H, J=9.2 Hz), 10.73(br, 1H)

EXAMPLE 42

5(3,3,3-Trifluoro-2-hydroxy-2-methylpropanoylamino)-4,10-dihydrofuro[2,3-c][1]benzothiepin-4-one (Compound 42) (yield:56%)

$^1$H-NMR (CDCl$_3$) δ:1.72(s, 3H), 3.97(s, 2H), 4.17(br, 1H), 6.87(d, 1H, J=2.0 Hz), 7.28(d, 1H, J=2.0 Hz), 7.43(t, 1H, J=7.9 Hz), 7.55(d, 1H, J=7.9 Hz), 8.32(d, 1H, J=7.9 Hz), 10.71(br, 1H)

EXAMPLE 43

7-(3,3,3-Trifluoro-2-hydroxy-2-methylpropanoylamino)-4,10-dihydrofuro[2,3-c][1]benzothiepin-4-one (Compound 43) (yield:70%)

$^1$H-NMR (DMSO-d$_6$) δ:1.60(s, 3H), 3.61(br, 1H), 4.24(s, 2H), 6.88(d, 1H, J=2.0 Hz), 7.65(d, 1H, J=2.0 Hz), 7.87(d, 1H, J=8.1 Hz), 7.94(d, 1H, J=8.1 Hz), 8.19(s, 1H), 10.30(br, 1H)

EXAMPLE 44

9-(3,3,3-Trifluoro-2-hydroxy-2-methylpropanoylamino)-4,10-dihydrothieno[3,2-c][1]benzothiepin-10-one (Compound 44) (yield:62%)

$^1$H-NMR (CDCl$_3$) δ:1.72(s, 3H), 3.98(s, 2H), 4.22(br, 1H), 6.97(d, 1H, J=5.0 Hz), 7.43(t, 1H, J=8.0 Hz), 7.51(d, 1H, J=8.0 Hz), 7.62(d, 1H, J=5.0 Hz), 8.27(d, 1H, J=8.0 Hz), 10.62(br, 1H)

EXAMPLE 45

7-(3,3,3-Trifluoro-2-hydroxy-2-methylpropanoylamino)-4,10-dihydrothieno[3,2-c][1]benzothiepin-10-one (Compound 45) (yield:99%)

$^1$H-NMR (DMSO-d$_6$) δ:1.60(s, 3H), 4.19(s, 2H), 7.17(d, 1H, J=5.0 Hz), 7.55(br, 1H), 7.87(d, 1H, J=8.9 Hz), 7.95(d, 1H, J=5.0 Hz), 7.98(d, 1H, J=8.9 Hz), 8.17(s, 1H), 10.71(br, 1H)

EXAMPLE 46

5-(3,3,3-Trifluoro-2-hydroxy-2-methylpropanoylamino)-4,10-dihydrothieno[2,3-c][1]benzothiepin-4-one (Compound 46) (yield:53%)

$^1$H-NMR (CDCl$_3$) δ:1.81(s, 3H), 4.46(br, 1H), 5.21(s, 2H), 7.34(d, 2H, J=7.4 Hz), 7.39(d, 1H, J=8.6 Hz), 7.45(t,

1H, J=7.4 Hz), 7.58(t, 1H, J=7.4 Hz), 7.87(d, 1H, J=7.4 Hz), 8.26(d, 1H, J=8.6 Hz), 12.57(br, 1H)

EXAMPLE 47

7-(3,3,3-Trifluoro-2-hydroxy-2-methylpropanoylamino)-4,10-dihydrothieno[2,3-c][1]benzothiepin-4-one (Compound 47) (yield:28%)

$^1$H-NMR (DMSO-d$_6$) δ:1.59(s, 3H), 4.39(s, 2H), 7.35(d, 1H, J=5.3 Hz), 7.51(d, 1H, J=5.3 Hz), 7.56(s, 1H), 7.86(dd, 1H, J=8.6, 2.0 Hz), 8.00(d, 1H, J=8.6 Hz), 8.14(d, 1H, J=2.0 Hz), 10.37(br, 1H)

EXAMPLE 48

5-Oxo-1-(3,3,3-trifluoro-2-hydroxy-2-methylpropanoylamino)-6,11-dihydrodibenzo[b,e]thiepin-11-one (Compound 48) (yield:55%)

$^1$H-NMR (DMSO-d$_6$) δ:1.53(s, 3H), 4.56(d, 1H, J=15.5 Hz), 4.92(d, 1H, J=15.5 Hz), 7.43(d, 1H, J=7.6 Hz), 7.52(t, 1H, J=7.6 Hz), 7.63–7.76(m, 3H), 7.89–8.02(m, 2H), 10.38 (br, 1H)

EXAMPLE 49

5-Oxo-3-(3,3,3-trifluoro-2-hydroxy-2-methylpropanoylamino)-6,11-dihydrodibenzo[b,e]thiepin-11-one (Compound 49) (yield:60%)

$^1$H-NMR (DMSO-d$_6$) δ:1.62 (s, 3H), 4.57(d, 1H, J=13.5 Hz), 4.98(d, 1H, J=13.5 Hz), 7.49–7.68(m, 4H), 8.00(d, 1H, J=8.3 Hz), 8.16(d, 1H, J=8.3 Hz), 8.49(s, 1H), 10.61(br, 1H)

EXAMPLE 50

9-Oxo-5-(3,3,3-trifluoro-2-hydroxy-2-methylpropanoylamino)-4,10-dihydrothieno[2,3-c][1]benzothiepin-4-one (Compound 50) (yield:64%)

$^1$H-NMR (DMSO-d$_6$) δ:1.55(s, 3H), 4.75(d, 1H, J=15.8 Hz), 4.93(d, 1H, J=15.8 Hz), 7.48(d, 1H, J=5.3 Hz), 7.60(d, 1H, J=5.3 Hz), 7.77(m, 3H), 8.19(d, 1H, J=8.6 Hz), 10.80(br, 1H)

EXAMPLE 51

9-Oxo-7-(3,3,3-trifluoro-2-hydroxy-2-methylpropanoylamino)-4,10-dihydrothieno[2,3-c][1]benzothiepin-4-one (Compound 51) (yield:62%)

$^1$H-NMR (DMSO-d$_6$) δ:1.61(s, 3H), 4.83(d, 1H, J=14.8 Hz), 4.96(d, 1H, J=14.8 Hz), 7.61(m, 3H), 7.97(d, 1H, J=8.6 Hz), 8.07(dd, 1H, J=8.6, 2.0 Hz), 8.50(d, 1H, J=2.0 Hz), 10.67(br, 1H)

EXAMPLE 52

4-(3,3,3-Trifluoro-2-hydroxy-2-methylpropanoylamino)-10,11-dihydro-5H-dibenzo[a,d]cyclohepten-5-one (Compound 52)

In dimethylacetamide (15 ml) was dissolved 3,3,3-trifluoro-2-hydroxy-2-methylpropionic acid (0.370 g, 2.37 mmol), and thionyl chloride (0.206 ml, 2.83 mmol) was added thereto at −5° C., followed by stirring at −5° C. for 2 hours. To this reaction mixture were added 4-amino-10,11-dihydro-5H-dibenzo[a,d]cyclohepten-5-one obtained substantially in the same manner as in Reference Examples 12 to 18 (0.210 g, 0.942 mmol) and triethylamine (0.394 ml, 2.83 mmol), followed by stirring at room temperature for 4 hours. After concentration of the reaction mixture under reduced pressure, the obtained residue was dissolved in ethyl acetate (20 ml). The organic layer was washed successively with a saturated aqueous solution of sodium bicarbonate and a saturated aqueous solution of sodium chloride, and then dried over anhydrous magnesium sulfate. After the drying agent was filtered off, the organic layer was concentrated under reduced pressure. The obtained oily residue was purified by silica gel column chromatography (hexane/ethyl acetate=5/1), followed by trituration with hexane to give Compound 52(0.210 g, 61%).

$^1$H-NMR (CDCl$_3$) δ:1.73(s, 3H), 3.10–3.35(br, 4H), 4.26 (br, 1H), 7.08(dd, 1H, J=7.6, 0.8 Hz), 7.21–7.32(m, 1H), 7.32–7.41(m, 1H), 7.41–7.52(m, 2H), 8.03(dd, 1H, J=7.9, 1.7 Hz), 8.16(dd, 1H, J=8.2, 0.8 Hz), 10.28(br, 1H)

In the following Examples 53 to 68, the substantially same procedure as in Example 52 was repeated except that the corresponding tricyclic aromatic amine was used instead of 4-amino-10,11-dihydro-5H-dibenzo[a,d]cyclohepten-5-one, to give the desired compound.

EXAMPLE 53

3-(3,3,3-Trifluoro-2-hydroxy-2-methylpropanoylamino)-10,11-dihydro-5H-dibenzo[a,d]cyclohepten-5-one (Compound 53) (yield:83%)

$^1$H-NMR (CDCl$_3$) δ:1.74(s, 3H), 3.20(br, 4H), 4.01(br, 1H), 7.21–7.28(m, 2H), 7.30–7.38(m, 1H), 7.42–7.50(m, 1H), 7.89(d, 1H, J=2.3 Hz), 7.95–8.03(m, 2H), 8.43(br, 1H)

EXAMPLE 54

2-(3,3,3-Trifluoro-2-hydroxy-2-methylpropanoylamino)-10,11-dihydro-5H-dibenzo[a,d]cyclohepten-5-one (Compound 54) (yield:54%)

$^1$H-NMR (CDCl$_3$) δ:1.76(s, 3H), 3.20(br, 4H), 3.77(br, 1H), 7.23(dd, 1H, J=7.3, 1.0 Hz), 7.31–7.50(m, 3H), 7.70(d, 1H, J=2.3 Hz), 8.02(dd, 1H, J=7.9, 1.7 Hz), 8.10(d, 1H, J=8.6 Hz), 8.51(br, 1H)

EXAMPLE 55

9-(3,3,3-Trifluoro-2-hydroxy-2-methylpropanoylamino)-4,5-dihydro-10H-benzo[5,6]cyclohepta[1,2-b]thiophen-10-one (Compound 55) (yield:80%)

$^1$H-NMR (CDCl$_3$) δ:1.75(s, 3H), 3.04–3.22(m, 4H), 4.39 (br, 1H), 6.96(d, 1H, J=5.2 Hz), 7.11(dd, 1H, J=8.0, 1.0 Hz), 7.48(t, 1H, J=8.0 Hz), 7.63(d, 1H, J=5.2 Hz), 8.38(dd, 1H, J=8.0, 1.0 Hz), 11.50(br, 1H)

EXAMPLE 56

7-(3,3,3-Trifluoro-2-hydroxy-2-methylpropanoylamino)-4,5-dihydro-10H-benzo[5,6]cyclohepta[1,2-b]thiophen-10-one (Compound 56) (yield:75%)

$^1$H-NMR (CDCl$_3$) δ:1.77(s, 3H), 3.06–3.21(m, 4H), 3.71 (br, 1H), 6.96(d, 1H, J=5.0 Hz), 7.37(dd, 1H, J=8.6, 2.2 Hz), 7.58(d, 1H, J=5.0 Hz), 7.77(d, 1H, J=2.2 Hz), 8.04(d, 1H, J=8.6 Hz), 8.52(br, 1H)

EXAMPLE 57

5-(3,3,3-Trifluoro-2-hydroxy-2-methylpropanoylamino)-9,10-dihydro-4H-benzo[4,5]cyclohepta[1,2-b]thiophen-4-one (Compound 57) (yield:76%)

$^1$H-NMR (CDCl$_3$) δ:1.74(s, 3H), 3.19–3.30(m, 4H), 4.34 (br, 1H), 7.07(d, 1H, J=5.3 Hz), 7.09(dd, 1H, J=8.0, 1.0 Hz), 7.45(t, 1H, J=8.0 Hz), 7.57(d, 1H, J=5.3 Hz), 8.31(dd, 1H, J=8.0, 1.0 Hz), 11.09(br, 1H)

EXAMPLE 58

7-(3,3,3-Trifluoro-2-hydroxy-2-methylpropanoylamino)-9,10-dihydro-4H-benzo[4,5]cyclohepta[1,2-b]furan-4-one (Compound 58) (yield:65%)

$^1$H-NMR (CDCl$_3$) δ:1.76(s, 3H), 3.09–3.21(m, 4H), 3.98 (br, 1H), 6.91(d, 1H, J=2.0 Hz), 7.30(d, 1H, J=2.0 Hz), 7.37(dd, 1H, J=8.4, 2.1 Hz), 7.76(d, 1H, J=2.1 Hz), 7.95(d, 1H, J=8.4 Hz), 8.55(br, 1H)

EXAMPLE 59

8-(3,3,3-Trifluoro-2-hydroxy-2-methylpropanoylamino)-10,11-dihydro-5H-benzo[4,5]cyclohepta[1,2-b]pyridin-5-one (Compound 59) (yield:25%)

$^1$H-NMR (CDCl$_3$) δ:1.76(s, 3H), 3.21–3.28(m, 2H), 3.42–3.49(m, 2H), 5.00(br, 1H), 7.33(dd, 1H, J=7.9, 4.9 Hz), 7.45(dd, 1H, J=8.6, 2.0 Hz), 7.72(d, 1H, J=2.0 Hz), 8.05(d, 1H, J=8.6 Hz), 8.42(dd, 1H, J=7.9, 1.7 Hz), 8.63(dd, 1H, J=4.9, 1.7 Hz), 8.74(br, 1H)

EXAMPLE 60

4-(3,3,3-Trifluoro-2-hydroxy-2-methylpropanoylamino)-5H-dibenzo[a,d]cyclohepten-5-one (Compound 60) (yield: 87%)

$^1$H-NMR (CDCl$_3$) δ:1.82(s, 3H), 4.35(br, 1H), 7.09(s, 2H), 7.39(dd, 1H, J=7.9, 1.2 Hz), 7.46–7.69(m, 4H), 7.95 (dd, 1H, J=7.6, 1.2 Hz), 8.45(dd, 1H, J=8.2, 1.2 Hz), 11.07(br, 1H)

EXAMPLE 61

3-(3,3,3-Trifluoro-2-hydroxy-2-methylpropanoylamino)-5H-dibenzo[a,d]cyclohepten-5-one (Compound 61) (yield:

$^1$H-NMR (CDCl$_3$) δ:1.77(s, 3H), 3.95(br, 1H), 7.06(s, 2H), 7.55–7.65(m, 3H), 7.66–7.73(m, 1H), 8.12(d, 1H, J=2.3 Hz), 8.23–8.31(m, 2H), 8.66(br, 1H)

EXAMPLE 62

2-(3,3,3-Trifluoro-2-hydroxy-2-methylpropanoylamino)-5H-dibenzo[a,d]cyclohepten-5-one (Compound 62) (yield: 91%)

$^1$H-NMR (CDCl$_3$) δ:1.79(s, 3H), 3.65(br, 1H), 7.02(d, 1H, J=12.2 Hz), 7.09(d, 1H, J=12.2 Hz), 7.54–7.62(m, 1H), 7.64–7.71(m, 1H), 8.01(d, 1H, J=2.0 Hz), 8.24–8.32(m, 2H), 8.59(br, 1H)

EXAMPLE 63

9-(3,3,3-Trifluoro-2-hydroxy-2-methylpropanoylamino)-10H-benzo[5,6]cyclohepta[1,2-b]thiophen-10-one (Compound 63) (yield:88%)

$^1$H-NMR (CDCl$_3$) δ:1.85(s, 3H), 4.50(br, 1H), 7.20–7.38 (m, 3H), 7.57(dd, 1H, J=8.2, 1.0 Hz), 7.77(t, 1H, J=8.2 Hz), 7.83(d, 1H, J=5.3 Hz), 8.97(dd, 1H, J=8.2, 1.0 Hz), 13.84(br, 1H)

EXAMPLE 64

8-(3,3,3-Trifluoro-2-hydroxy-2-methylpropanoylamino)-10H-benzo[5,6]cyclohepta[1,2-b]thiophen-10-one (Compound 64) (yield:95%)

$^1$H-NMR (DMSO-d$_6$) δ:1.69(s, 3H), 7.49(d, 1H, J=11.9 Hz), 7.55(d, 1H, J=11.9 Hz), 7.66(d, 1H, J=5.3 Hz), 8.03(d, 1H, J=8.6 Hz), 8.26(d, 1H, J=5.3 Hz), 8.31(dd, 1H, J=8.6, 2.1 Hz), 9.17(d, 1H, J=2.1 Hz), 10.59(br, 1H)

EXAMPLE 65

7-(3,3,3-Trifluoro-2-hydroxy-2-methylpropanoylamino)-10H-benzo[5,6]cyclohepta[1,2-b]thiophen-10-one (Compound 65) (yield:84%)

$^1$H-NMR (DMSO-d$_6$) δ:1.69(s, 3H), 7.43(d, 1H, J=11.6 Hz), 7.55(d, 1H, J=11.6 Hz), 7.67(d, 1H, J=5.3 Hz), 7.71(br, 1H), 8.11–8.27(m, 2H), 8.47(d, 1H, J=2.0 Hz), 8.67(d, 1H, J=9.3 Hz), 10.58(br, 1H)

EXAMPLE 66

5-(3,3,3-Trifluoro-2-hydroxy-2-methylpropanoylamino)-4H-benzo[4,5]cyclohepta[1,2-b]thiophen-4-one (Compound 66) (yield:90%)

$^1$H-NMR (CDCl$_3$) δ:1.83(s, 3H), 4.48(br, 1H), 7.18(d, 1H, J=11.9 Hz), 7.26(d, 1H, J=11.9 Hz), 7.44(d, 1H, J=5.4 Hz), 7.51(dd, 1H, J=7.9, 1.3 Hz), 7.71(t, 1H, J=7.9 Hz), 7.83(d, 1H, J=5.4 Hz), 8.75(dd, 1H, J=7.9, 1.3 Hz), 12.83(br, 1H)

EXAMPLE 67

9-(3,3,3-Trifluoro-2-hydroxy-2-methylpropanoylamino)-10H-benzo[5,6]cyclohepta[1,2-b]furan-10-one (Compound 67) (yield:81%)

$^1$H-NMR (CDCl$_3$) δ:1.87(s, 3H), 4.56(br, 1H), 6.84(d, 1H, J=1.8 Hz), 7.17(d, 1H, J=11.5 Hz), 7.43(d, 1H, J=11.5 Hz), 7.61(dd, 1H, J=8.1, 1.3 Hz), 7.80(t, 1H, J=8.1 Hz), 7.91(d, 1H, J=1.8 Hz), 9.05(dd, 1H, J=8.1, 1.3 Hz), 14.23(br, 1H)

EXAMPLE 68

7-(3,3,3-Trifluoro-2-hydroxy-2-methylpropanoylamino)-10H-benzo[5,6]cyclohepta[1,2-b]furan-10-one (Compound 68) (yield:85%)

$^1$H-NMR (DMSO-d$_6$) δ:1.63(s, 3H), 7.12(d, 1H, J=1.8 Hz), 7.32(d, 1H, J=11.8 Hz), 7.41(d, 1H, J=11.8 Hz), 7.63 (br, 1H), 8.17(dd, 1H, J=8.9, 2.0 Hz), 8.25(d, 1H, J=1.8 Hz), 8.41(d, 1H, J=2.0 Hz), 8.71(d, 1H, J=8.9 Hz), 10.47(br, 1H)

EXAMPLE 69

8-Chloro-7-(3,3,3-trifluoro-2-hydroxy-2-methylpropanoylamino)-4,10-dihydrothieno[3,2-c][1]-benzoxepin-10-one (Compound 69) (yield:95%)

$^1$H-NMR (DMSO-d$_6$) δ:1.63(s, 3H), 5.35(s, 2H), 7.25(d, 1H, J=5.0 Hz), 8.07(d, 1H, J=5.0 Hz), 8.11(s, 1H), 8.13(s, 1H), 8.15(s, 1H), 9.85(br, 1H)

EXAMPLE 70

7-Methyl-8-(3,3,3-trifluoro-2-hydroxy-2-methylpropanoylamino)-4,10-dihydrothieno[3,2-c][1]-benzoxepin-10-one (Compound 70) (yield:51%)

$^1$H-NMR (DMSO-d$_6$) δ:1.59(s, 3H), 2.22(s, 3H), 5.29(s, 2H), 7.12(s, 1H), 7.25(d, 1H, J=5.0 Hz), 7.42(br, 1H), 7.94(s, 1H), 8.06(d, 1H, J=5.0 Hz), 9.75(br, 1H)

EXAMPLE 71

7-Methyl-9-(3,3,3-trifluoro-2-hydroxy-2-methylpropanoylamino)-5,11-dihydropyrido[2,3-c][1]-benzoxepin-5-one (Compound 71) (yield:64%)

$^1$H-NMR (CDCl$_3$) δ:1.77(s, 3H), 2.40(s, 3H), 5.48(s, 2H), 5.59(br, 1H), 7.53(dd, 1H, J=7.9, 4.9 Hz), 7.81(d, 1H, J=2.3

Hz), 8.37(dd, 1H, J=7.9, 1.7 Hz), 8.57(d, 1H, J=2.3 Hz), 8.72(dd, 1H, J=4.9, 1.7 Hz), 9.30(br, 1H)

EXAMPLE 72

9-(3,3,3-Trifluoro-2-hydroxy-2-methylpropanoylamino)-4,5-dihydro-10H-benzo[5,6]cyclohepta[1,2-b]furan-10-one (Compound 72) (yield:63%)

$^1$H-NMR (CDCl$_3$) δ:1.77(s, 3H), 2.87–2.96(m, 2H), 3.13–3.22(m, 2H), 4.34(br, 1H), 6.46(d, 1H, J=1.7 Hz), 7.10(dd, 1H, J=8.0, 1.0 Hz), 7.48(t, 1H, J=8.0 Hz), 7.64(d, 1H, J=1.7 Hz), 8.48(dd, 1H, J=8.0, 1.0 Hz), 11.94(br, 1H)

EXAMPLE 73

7-(3,3,3-Trifluoro-2-hydroxy-2-methylpropanoylamino)-4,5-dihydro-10H-benzo[5,6]cyclohepta[1,2-b]furan-10-one (Compound 73) (yield:88%)

$^1$H-NMR (CDCl$_3$) δ:1.77(s, 3H), 2.89–2.98(m, 2H), 3.12–3.20(m, 2H), 4.04(br, 1H), 6.44(d, 1H, J=1.7 Hz), 7.37(dd, 1H, J=8.6, 2.0 Hz), 7.61(d, 1H, J=1.7 Hz), 7.79(d, 1H, J=2.0 Hz), 8.10(d, 1H, J=8.6 Hz), 8.60(br, 1H)

EXAMPLE 74

7-(3,3,3-Trifluoro-2-hydroxy-2-methylpropanoylamino)-5H-benzo[4,5]cyclohepta[1,2-b]pyridin-5-one (Compound 74) (yield:70%)

$^1$H-NMR (CDCl$_3$) δ:1.77(s, 3H), 7.27(d, 1H, J=12.5 Hz), 7.36(d, 1H, J=12.5 Hz), 7.49(dd, 1H, J=7.9, 4.6 Hz), 7.65(d, 1H, J=8.3 Hz), 8.22(d, 1H, J=2.4 Hz), 8.27(dd, 1H, J=8.3, 2.4 Hz), 8.56(dd, 1H, J=7.9, 1.6 Hz), 8.69(br, 1H), 8.91(dd, 1H, J=4.6, 1.6 Hz)

EXAMPLE 75

9-(3,3,3-Trifluoro-2-hydroxy-2-methylpropanoylamino)-5H-benzo[4,5]cyclohepta[1,2-b]pyridin-5-one (Compound 75) (yield:65%)

$^1$H-NMR (CDCl$_3$) δ:1.88(s, 3H), 7.40(d, 1H, J=12.7 Hz), 7.49(d, 1H, J=12.7 Hz), 7.57(dd, 1H, J=8.3, 5.0 Hz), 7.65(t, 1H, J=7.9 Hz), 7.98(dd, 1H, J=7.9, 1.3 Hz), 8.24(dd, 1H, J=7.9, 1.3 Hz), 8.42(dd, 1H, J=8.3, 1.7 Hz), 8.84(dd, 1H, J=5.0, 1.7 Hz), 9.07 (br, 1H)

EXAMPLE 76

7-(3,3,3-Trifluoro-2-hydroxy-2-methylpropanoylamino)-10,11-dihydro-5H-benzo[4,5]cyclohepta[1,2-b]pyridin-5-one (Compound 76) (yield:40%)

$^1$H-NMR (DMSO-d$_6$) δ:1.58(s, 3H), 3.13–3.27(m, 2H), 3.30–3.44(m, 2H), 7.35(d, 1H, J=8.3 Hz), 7.45(br, 1H), 7.46(dd, 1H, J=7.9, 4.6 Hz), 7.85(dd, 1H, J=8.3, 2.4 Hz), 8.28(d, 1H, J=2.4 Hz), 8.29(dd, 1H, J=7.9, 1.6 Hz), 8.67(dd, 1H, J=4.6, 1.6 Hz), 10.16(br, 1H)

EXAMPLE 77

9-(3,3,3-Trifluoro-2-hydroxy-2-methylpropanoylamino)-10,11-dihydro-5H-benzo[4,5]cyclohepta[1, 2-b]pyridin-5-one (Compound 77) (yield:45%)

$^1$H-NMR (CDCl$_3$) δ:1.80(s, 3H), 3.15–3.26(m, 2H), 3.44–3.54(m, 2H), 7.37–7.45(m, 2H), 7.78(dd, 1H, J=7.9, 1.3 Hz), 8.04(dd, 1H, J=7.9, 1.3 Hz), 8.29(dd, 1H, J=7.9, 1.7 Hz), 8.60(dd, 1H, J=5.0, 1.7 Hz), 8.84(br, 1H)

Reference Example 1

Methyl 2-(3-acetamidophenoxymethyl)benzoate

To a solution of 3-acetamidophenol (1.0 g, 6.6 mmol) in dimethylformamide (10 ml) was added cesium carbonate (1.3 g, 3.9 mmol), followed by stirring at room temperature for 30 minutes. To the resulting mixture was added methyl 2-bromomethylbenzoate (1.8 g, 7.9 mmol), and the mixture was stirred overnight at room temperature. After the reaction was completed, the reaction mixture was poured into a 5% aqueous solution of sodium bicarbonate, followed by extraction with ethyl acetate. The organic layer was washed with a saturated aqueous solution of sodium chloride, and then dried over anhydrous magnesium sulfate. After the drying agent was filtered off, the organic layer was concentrated under reduced pressure. The obtained oily substance was purified by silica gel column chromatography (hexane/ethyl acetate=4/1), followed by trituration with hexane to give methyl 2-(3-acetamidophenoxymethyl)benzoate as a white solid (1.21 g, 61%).

$^1$H-NMR (CDCl$_3$) δ:2.16(s, 3H), 3.90(s, 3H), 5.47(s, 2H), 6.73(d, 1H, J=7.8 Hz), 7.09(d, 1H, J=7.8 Hz), 7.07–7.26(m, 1H), 7.34(s, 1H), 7.38(d, 1H, J=7.8 Hz), 7.55(t, 1H, J=7.8 Hz), 7.73(d, 1H, J=7.8 Hz), 8.15(d, 1H, J=7.8 Hz)

Reference Example 2

2-(3-Acetamidophenoxymethyl)benzoic acid

The methyl ester obtained in Reference Example 1(1.0 g, 3.4 mmol) was dissolved in methanol (25 ml), and a 2N aqueous solution of sodium hydroxide (25 ml) was added thereto, followed by stirring at room temperature for 2 hours. After the reaction was completed, methanol was distilled off under reduced pressure, and the resulting mixture was adjusted to pH 3 with concentrated hydrochloric acid. The precipitated white solid was washed well with water and dried to give 2-(3-acetamidophenoxymethyl)benzoic acid (0.87 g, 90%).

$^1$H-NMR (DMSO-d$_6$) δ:2.02(s, 3H), 5.42(s, 2H), 6.64(d, 1H, J=7.8 Hz), 7.13–7.22(m, 2H), 7.31(s, 1H), 7.43(t, 1H, J=7.8 Hz), 7.56–7.65(m, 2H), 7.94(d, 1H, J=7.8 Hz), 9.92 (br, 1H), 13.02(br, 1H)

Reference Example 3

1-Acetamido-6,11-dihydrodibenz[b,e]oxepin-11-one [1]

3-Acetamido-6,11-dihydrodibenz[b,e]oxepin-11-one [2]

The carboxylic acid obtained in Reference Example 2 (1.6 g, 5.6 mmol) was suspended in dichloromethane (20 ml), and trifluoroacetic anhydride (0.95 ml, 6.7 mmol) was added dropwise thereto under ice cooling, followed by stirring at room temperature for 2 hours. After the reaction mixture was ice cooled again, boron trifluoride diethyl etherate (0.5 equivalent) was added thereto, and the mixture was stirred overnight at room temperature. After the reaction was completed, the dichloromethane layer was washed successively with water, a 5% aqueous solution of sodium bicarbonate, and a saturated aqueous solution of sodium chloride, and then dried over anhydrous magnesium sulfate. After the drying agent was filtered off, the organic layer was concentrated under reduced pressure. The obtained oily mixture was separated and purified by silica gel column chromatography (chloroform/methanol=100/1) to give 1-acetamido-6,11-dihydrodibenz[b,e]oxepin-11-one[1](0.31 g, 21%) and 3-acetamido-6,11-dihydrodibenz[b,e]oxepin-11-one[2](0.28 g, 19%), respectively.

[1] $^1$H-NMR (CDCl$_3$) δ:2.28(s, 3H), 5.15(s, 2H), 6.79(d, 1H, J=7.8 Hz), 7.32(d, 1H, J=7.8 Hz), 7.45–7.58(m, 3H), 7.84(d, 1H, J=7.8 Hz), 8.41(d, 1H, J=7.8 Hz)

[2] $^1$H-NMR (CDCl$_3$) δ:2.20(s, 3H), 5.19(s, 2H), 7.10(d, 1H, J=8.0 Hz), 7.36(d, 1H, J=8.0 Hz), 7.49–7.58(m, 3H), 7.91(d, 1H, J=8.0 Hz), 8.21(d, 1H, J=8.0 Hz)

Reference Example 4

1-Amino-6,11-dihydrodibenz[b,e]oxepin-11-one

In concentrated hydrochloric acid (10 ml), 1-acetamido-6,11-dihydrodibenz[b,e]oxepin-11-one obtained in Reference Example 3(0.25 g, 0.94 mmol) was heated under reflux for 2 hours. The reaction mixture was poured into a saturated aqueous solution of sodium bicarbonate, followed by extraction with ethyl acetate (25 ml). The organic layer was washed with a saturated aqueous solution of sodium chloride, and then dried over anhydrous magnesium sulfate. After the drying agent was filtered off, the organic layer was concentrated under reduced pressure to give 1-amino-6,11-dihydrodibenz[b,e]oxepin-11-one as a yellow solid (0.17 g, 81%).

$^1$H-NMR (CDCl$_3$) δ:5.12(s, 2H), 6.11(d, 1H, J=8.1 Hz), 6.47(d, 1H, J=8.1 Hz), 7.12(t, 1H, J=8.1 Hz), 7.42–7.55(m, 3H), 7.73(d, 1H, J=8.1 Hz)

Reference Example 5

3-Amino-6,11-dihydrodibenz[b,e]oxepin-11-one

Substantially the same procedure as in Reference Example 4 was repeated using 3-acetamido-6,11-dihydrodibenz[b,e]oxepin-11-one obtained in Reference Example 3 instead of 1-acetamido-6,11-dihydrodibenz[b,e]oxepin-11-one to give 3-amino-6,11-dihydrodibenz[b,e]oxepin-11-one as a white solid (yield:95%).

$^1$H-NMR (CDCl$_3$) δ:3.85(br, 2H), 5.05(s, 2H), 6.11(s, 1H), 6.31(d, 1H, J=7.9 Hz), 7.23(d, 1H, J=7.9 Hz), 7.33–7.45(m, 2H), 7.85(d, 1H, J=7.9 Hz), 8.04(d, 1H, J=7.9 Hz)

Reference Example 6

2-Amino-6,11-dihydrodibenz[b,e]oxepin-11-one

To tert-butanol (8.3 ml) were added diphenylphosphoryl azide (1.1 ml, 5.11 mmol), 2-carboxy-6,11-dihydrodibenz[b,e]oxepin-11-one (Japanese Published Unexamined Patent Application No. 91040/90) (1.0 g, 3.9 mmol), and triethylamine (0.71 ml, 5.11 mmol) under an atmosphere of argon gas, followed by heating under reflux for 2 hours. After the reaction mixture was cooled, it was poured into a 5% aqueous solution of sodium bicarbonate, followed by extraction with ethyl acetate. The organic layer was washed with a saturated aqueous solution of sodium chloride, and then dried over anhydrous magnesium sulfate. After the drying agent was filtered off, the organic layer was concentrated under reduced pressure. The obtained oily substance was purified by silica gel column chromatography (hexane/ethyl acetate=8/1), followed by trituration with hexane to give 2-tert-butoxycarbonylamino-6,11-dihydrodibenz[b,e]oxepin-11-one as a white solid (0.51 g, 41%).

$^1$H-NMR (CDCl$_3$) δ:1.49(s, 9H), 5.23(s, 2H), 7.21–7.26 (m, 2H), 7.48–7.54(m, 2H), 7.60–7.65(m, 1H), 7.80(d, 1H, J=8.2 Hz), 8.02(d, 1H, J=8.2 Hz), 9.80(br, 1H)

To the obtained white solid (0.41 g) was added 4N hydrochloric acid/dioxane (10 ml), followed by stirring at room temperature for one hour. The reaction mixture was concentrated under reduced pressure to give 2-amino-6,11-dihydrodibenz[b,e]oxepin-11-one as a white solid. This product was used for the synthesis of Compound 3 without purification.

Reference Example 7

Methyl 3-(3-acetamidophenoxymethyl)-2-thiophenecarboxylate

To a solution of 3-acetamidophenol (4.79 g, 31.7 mmol) in dimethylformamide (50 ml) was added cesium carbonate (5.67 g, 17.4 mmol), followed by stirring at room temperature for 30 minutes. To the resulting mixture was added methyl 3-bromomethyl-2-thiophenecarboxylate (8.94 g, 38.0 mmol), and the mixture was stirred overnight at room temperature. After the reaction was completed, the reaction mixture was poured into a 5% aqueous solution of sodium bicarbonate, followed by extraction with ethyl acetate. The organic layer was washed with a saturated aqueous solution of sodium chloride, and then dried over anhydrous magnesium sulfate. After the drying agent was filtered off, the organic layer was concentrated under reduced pressure. The obtained oily substance was purified by silica gel column chromatography (hexane/ethyl acetate=5/1), followed by trituration with hexane to give methyl 3-(3-acetamidophenoxymethyl)-2-thiophenecarboxylate as a white solid (7.27 g, 75%).

$^1$H-NMR (CDCl$_3$) δ:2.17(s, 3H), 3.94(s, 3H), 5.45(s, 2H), 6.72(d, 1H, J=8.1 Hz), 7.07(d, 1H, J=8.1 Hz), 7.18–7.24(m, 2H), 7.29(d, 1H, J=5.1 Hz), 7.48(d, 1H, J=5.1 Hz)

Reference Example 8

3-(3-Acetamidophenoxymethyl)-2-thiophenecarboxylic acid

The methyl ester obtained in Reference Example 7(6.27 g, 20.5 mmol) was dissolved in methanol (100 ml), and a2N aqueous solution of sodium hydroxide (50 ml) was added thereto, followed by stirring at room temperature for 2 hours. After the reaction was completed, methanol was distilled off under reduced pressure, and the resulting mixture was adjusted to pH 3 with concentrated hydrochloric acid. The precipitated white solid was washed well with water and dried to give 3-(3-acetamidophenoxymethyl)-2-thiophenecarboxylic acid (4.33 g, 73%).

$^1$H-NMR (DMSO-d$_6$) δ:2.02(s, 3H), 5.38(s, 2H), 6.62(d, 1H, J=8.1 Hz), 7.13–7.20(m, 2H), 7.23(d, 1H, J=5.1 Hz), 7.31(s, 1H), 7.78(d, 1H, J=5.1 Hz)

Reference Example 9

7-Acetamido-4,10-dihydrothieno[3,2-c][1]benzoxepin-10-one [1]

9-Acetamido-4,10-dihydrothieno[3,2-c][1]benzoxepin-10-one [2]

The carboxylic acid obtained in Reference Example 8 (2.20 g, 7.55 mmol) was suspended in dichloromethane (20 ml), and trifluoroacetic anhydride (1.28 ml, 9.66 mmol) was added dropwise thereto under ice cooling, followed by stirring at room temperature for 2 hours. After the reaction mixture was ice cooled again, boron trifluoride diethyl etherate (0.5 equivalent) was added thereto, and the mixture was stirred overnight at room temperature. After the reaction was completed, the dichloromethane layer was washed successively with water, a 5% aqueous solution of sodium bicarbonate, and a saturated aqueous solution of sodium chloride, and then dried over anhydrous magnesium sulfate. After the drying agent was filtered off, the organic layer was concentrated under reduced pressure. The obtained oily mixture was separated and purified by silica gel column chromatography (chloroform/methanol=100/1) to give 7-acetamido-4,10-dihydrothieno[3,2-c][1]benzoxepin-10-one [1] (0.42 g, 21%) and 9-acetamido-4,10-dihydrothieno-[3,2-c][1]benzoxepin-10-one [2] (0.28 g, 14%), respectively.

[1]$^1$H-NMR (CDCl$_3$) δ:2.10(s, 3H), 5.27(s, 2H), 7.22(d, 1H, J=5.3 Hz), 7.36(d, 1H, J=8.6 Hz), 7.58(s, 1H), 7.97–8.00 (m, 2H), 10.33(br, 1H)

[2]$^1$H-NMR (CDCl$_3$) δ:2.23(s, 3H), 5.16(s, 2H), 6.92(d, 1H, J=8.2 Hz), 6.98(d, 1H, J=5.1 Hz), 7.47(t, 1H, J=8.2 Hz), 7.69(d, 1H, J=5.1 Hz), 8.40(d, 1H, J=8.2 Hz), 11.28(br, 1H)

Reference Example 10

7-Amino-4,10-dihydrothieno[3,2-c][1]benzoxepin-10-one

In concentrated hydrochloric acid (15 ml), 7-acetamido-4,10-dihydrothieno[3,2-c][1]benzoxepin-10-one obtained in Reference Example 9(0.41 g, 1.51 mmol) was heated under reflux for 2 hours. The reaction mixture was poured into a saturated aqueous solution of sodium bicarbonate, followed by extraction with ethyl acetate (25 ml). The organic layer was washed with a saturated aqueous solution of sodium chloride, and then dried over anhydrous magnesium sulfate. After the drying agent was filtered off, the organic layer was concentrated under reduced pressure to give 7-amino-4,10-dihydrothieno[3,2-c][1]benzoxepin-10-one as a yellow solid (0.28 g, 78%).

$^1$H-NMR (CDCl$_3$) δ:4.22(br, 2H), 5.14(s, 2H), 6.31(s, 1H), 6.48(d, 1H, J=8.6 Hz), 6.99(d, 1H, J=5.0 Hz), 7.57(d, 1H, J=5.0 Hz), 8.08(d, 1H, J=8.6 Hz)

Reference Example 11

9-Amino-4,10-dihydrothieno[3,2-c][1]benzoxepin-10-one

Substantially the same procedure as in Reference Example 10 was repeated using 9-acetamido-4,10-dihydrothieno[3,2-c][1]benzoxepin-10-one obtained in Reference Example 9 (0.28 g, 1.02 mmol) instead of 7-acetamido-4,10-dihydrothieno[3,2-c][1]benzoxepin-10-one to give 9-amino-4,10-dihydrothieno[3,2-c][1]benzoxepin-10-one as a white solid (0.24 g, 99%).

$^1$H-NMR (CDCl$_3$) δ:5.11(s, 2H), 6.36(br, 2H), 6.41(d, 1H, J=7.9 Hz), 6.47(d, 1H, J=7.9 Hz), 6.95(d, 1H, J=5.0 Hz), 7.17(t, 1H, J=7.9 Hz), 7.58(d, 1H, J=5.0 Hz)

Reference Example 12

2-Methoxycarbonylthiophen-3-ylmethyltriphenylphosphonium bromide

To a solution of methyl 3-bromomethyl-2-thiophenecarboxylate (7.31 g, 31.1 mmol) in toluene (90 ml) was added triphenylphosphine (7.92 g, 30.2 mmol) under ice cooling. The temperature of the mixture was raised to room temperature, followed by stirring for 2 days. The precipitated crystals were collected by filtration and dried to give 2-methoxycarbonylthiophen-3-ylmethyltriphenylphosphonium bromide (10.57 g, 70.4%). This product was subjected to the reaction of Reference Example 13 without purification.

Reference Example 13

Methyl (E)-3-(3-nitrostyryl)-2-thiophenecarboxylate [1]

Methyl (Z)-3-(3-nitrostyryl)-2-thiophenecarboxylate [2]

To a solution of the phosphonium salt obtained in Reference Example 12 (2.26 g, 4.54 mmol) in tetrahydrofuran (30 ml) was added sodium hydride (0.131 g, 5.45 mmol) under an atmosphere of argon gas at 0° C., followed by stirring at room temperature for 3 hours. To the resulting mixture was added 3-nitrobenzaldehyde (0.527 g, 3.49 mmol) at 0° C., and the mixture was stirred overnight at room temperature. After the reaction was completed, the reaction mixture was poured into an aqueous solution of ammonium chloride, followed by extraction with ethyl acetate. The organic layer was washed successively with water and a saturated aqueous solution of sodium chloride, and then dried over anhydrous magnesium sulfate. After the drying agent was filtered off, the organic layer was concentrated under reduced pressure. The obtained residue was separated and purified by silica gel column chromatography (hexane/ethyl acetate=20/1) to give [1] (0.48 g, 47.5%) and [2] (0.37 g, 36.6%), respectively.

[1]$^1$H-NMR (CDCl$_3$) δ:3.93(s, 3H), 7.14(d, 1H, J=16.5 Hz), 7.46(d, 1H, J=5.4 Hz), 7.49(d, 1H, J=5.4 Hz), 7.54(t, 1H, J=8.2 Hz), 7.90(d, 1H, J=8.2 Hz), 8.09–8.16(m, 1H), 8.25(d, 1H, J=16.5 Hz), 8.32–8.37(m, 1H)

[2]$^1$H-NMR (CDCl$_3$) δ:3.91(s, 3H), 6.68(d, 1H, J=5.1 Hz), 6.76(d, 1H, J=12.2 Hz), 7.24(d, 1H, J=12.2 Hz), 7.30(d, 1H, J=5.1 Hz), 7.33–7.43(m, 2H), 8.00–8.10(m, 2H)

Reference Example 14

Methyl 3-(3-trimethylacetamidostyryl)-2-thiophenecarboxylate

A mixture of the (E) form and the (Z) form obtained in Reference Example 13 (2.56 g, 8.84 mmol) was suspended in a mixed solvent of ethanol (50 ml) and water (5 ml), and reduced iron (2.50 g) and iron (III) chloride (0.250 g) were added thereto, followed by stirring under heating under reflux for 20 minutes. After the reaction was completed, the solid was filtered off, followed by washing with ethyl acetate. To the filtrate was added a2N aqueous solution of sodium hydroxide (pH 9), and the organic layer was washed with a saturated aqueous solution of sodium chloride, and then dried over anhydrous magnesium sulfate. After the drying agent was filtered off, the organic layer was concentrated under reduced pressure to give methyl 3-(3-aminostyryl)-2-thiophenecarboxylate as a crude product. This product was dissolved in dichloromethane (50 ml) without purification, and triethylamine (1.79 g, 17.7 mmol) and trimethylacetyl chloride (2.13 g, 17.7 mmol) were added thereto at 0° C. The temperature of the mixture was raised to room temperature, followed by stirring for 2 hours. The obtained reaction mixture was poured into an aqueous solution of sodium bicarbonate. The organic layer was washed with a saturated aqueous solution of sodium bicarbonate, and then dried over anhydrous magnesium sulfate. After the drying agent was filtered off, the organic layer was concentrated under reduced pressure. The obtained residue was purified by silica gel column chromatography (hexane/ethyl acetate=10/1) to give methyl 3-(3-trimethylacetamidostyryl)-2-thiophenecarboxylate as an E/Z mixture. This mixture was subjected to the reaction of Reference Example 15 without further purification.

Reference Example 15

Methyl 3-[2-(3-trimethylacetamidophenyl)ethyl]-2-thiophenecarboxylate

The E/Z mixture of the amide obtained in Reference Example 14 was dissolved in a mixed solvent of ethanol (30 ml) and acetic acid (10 ml), and 10% palladium/carbon (moisture content:50%, 1.5 g) was added thereto under an atmosphere of argon gas, followed by replacement by hydrogen and heating under reflux for 2 hours. After the reaction mixture was cooled to room temperature, the solid was filtered off and washed with ethyl acetate. The obtained organic layer was washed successively with water and a saturated aqueous solution of sodium bicarbonate, and then dried over anhydrous magnesium sulfate. After the drying agent was filtered off, the organic layer was concentrated under reduced pressure. The obtained residue was triturated with hexane to give methyl 3-[2-(3-trimethylacetamidophenyl)ethyl]-2-thiophenecarboxylate (2.55 g, 3 steps, 83.5%).

$^1$H-NMR (CDCl$_3$) δ:1.32(s, 9H), 2.84–2.93(m, 2H), 3.25–3.34(m, 2H), 3.87(s, 3H), 6.89(d, 1H, J=5.0 Hz), 6.96(br d, 1H, J=7.6 Hz), 7.23(t, 1H, J=7.6 Hz), 7.30(br, 1H), 7.31–7.48(m, 3H)

Reference Example 16

3-[2-(3-Trimethylacetamidophenyl)ethyl]-2-thiophenecarboxylic acid

The methyl ester obtained in Reference Example 15 (2.40 g, 6.95 mmol) was dissolved in methanol (20 ml), and a 1N aqueous solution of sodium hydroxide (20 ml) was added thereto, followed by heating under reflux for 150 minutes. After the reaction was completed, methanol was distilled off under reduced pressure and the resulting mixture was adjusted to pH 3 with 2N hydrochloric acid. The resulting mixture was extracted three times with ethyl acetate, and the extract was washed with a saturated aqueous solution of sodium chloride and then dried over anhydrous sodium sulfate. After the drying agent was filtered off, the organic layer was concentrated under reduced pressure. The obtained residue was triturated with diisopropyl ether to give 3-[2-(3-trimethylacetamidophenyl)ethyl]-2-thiophenecarboxylic acid (2.06 g, 89.5%).

$^1$H-NMR (DMSO-d$_6$) δ:1.28(s, 9H), 2.83–2.92(m, 2H), 3.23–3.32(m, 2H), 6.97(br d, 1H, J=7.8 Hz), 7.15(d, 1H, J=5.0 Hz), 7.25(t, 1H, J=7.8 Hz), 7.55(br d, 1H, J=7.8 Hz), 7.60(br, 1H), 7.78(d, 1H, J=5.0 Hz), 9.91(br, 1H), 13.00(br, 1H)

Reference Example 17

7-Trimethylacetamido-4,5-dihydro-10H-benzo[5,6]cyclohepta[1,2-b]thiophen-10-one [1]

9-Trimethylacetamido-4,5-dihydro-10H-benzo[5,6]cyclohepta[1,2-b]thiophen-10-one [2]

The carboxylic acid obtained in Reference Example 16 (1.90 g, 5.73 mmol) was suspended in dichloromethane (10 ml), and trifluoroacetic anhydride (1.46 ml, 10.3 mmol) was added dropwise thereto under ice cooling, followed by stirring at room temperature for one hour. After this reaction mixture was ice cooled again, boron trifluoride diethyl etherate (0.7 equivalent) was added thereto, and the mixture was stirred overnight at room temperature. The reaction mixture was poured into 2N hydrochloric acid and the resulting mixture was stirred at room temperature for one hour, followed by extraction with ethyl acetate. The organic layer was washed twice with an aqueous solution of sodium bicarbonate and once with a saturated aqueous solution of sodium chloride successively, and then dried over anhydrous magnesium sulfate. After the drying agent was filtered off, the organic layer was concentrated under reduced pressure. The obtained mixture was separated and purified by silica gel column chromatography (hexane/ethyl acetate=20/1) to give [1] (0.56 g, 31.2%) and [2] (0.24 g, 13.4%), respectively.

[1] $^1$H-NMR (CDCl$_3$) δ:1.34(s, 9H), 3.03–3.20(m, 4H), 6.94(d, 1H, J=5.0 Hz), 7.28(dd, 1H, J=8.6, 2.3 Hz), 7.47(br, 1H), 7.56(d, 1H, J=5.0 Hz), 7.80(d, 1H, J=2.3 Hz), 8.02(d, 1H, J=8.6 Hz)

[2] $^1$H-NMR (CDCl$_3$) δ:1.32(s, 9H), 3.00–3.20(m, 4H), 6.93(d, 1H, J=5.3 Hz), 6.97(dd, 1H, J=8.0, 0.9 Hz), 7.40(t, 1H, J=8.0 Hz), 7.57(d, 1H, J=5.3 Hz), 8.40(dd, 1H, J=8.0, 0.9 Hz), 10.86(br, 1H)

Reference Example 18

7-Amino-4,5-dihydro-10H-benzo[5,6]cyclohepta[1,2-b]thiophen-10-one

In ethanol (10 ml) was suspended 7-trimethylacetamido-4,5-dihydro-10H-benzo[5,6]cyclohepta[1,2-b]thiophen-10-one obtained in Reference Example 17 (0.40 g, 1.28 mmol), and 6N hydrochloric acid (5 ml) was added thereto, followed by heating under reflux for 6 hours. After the reaction was completed, ethanol was distilled off under reduced pressure, and the resulting mixture was adjusted to pH 10 with an aqueous solution of sodium hydroxide. The mixture was extracted with dichloromethane, and the organic layer was washed with a saturated aqueous solution of sodium bicarbonate and then dried over anhydrous magnesium sulfate. After the drying agent was filtered off, the organic layer was concentrated under reduced pressure to give 7-amino-4,5-dihydro-10H-benzo[5,6]cyclohepta[1,2-b]thiophen-10-one (0.29 g, 98.8%).

$^1$H-NMR (CDCl$_3$) δ:3.06(br, 4H), 6.48(d, 1H, J=2.3 Hz), 6.62(dd, 1H, J=8.6, 2.3 Hz), 6.92(d, 1H, J=5.1 Hz), 7.51(d, 1H, J=5.1 Hz), 7.96(d, 1H, J=8.6 Hz)

Reference Example 19

9-Amino-4,5-dihydro-10H-benzo[5,6]cyclohepta[1,2-b]thiophen-10-one

Substantially the same procedure as in Reference Example 18 was repeated using 9-trimethylacetamido-4,5-dihydro-10H-benzo[5,6]cyclohepta[1,2-b]thiophen-10-one obtained in Reference Example 17 to give 9-amino-4,5-dihydro-10H-benzo[5,6]cyclohepta[1,2-b]thiophen-10-one (99.9%).

$^1$H-NMR (CDCl$_3$) δ:3.00–3.18(m, 4H), 6.52(d, 1H, J=7.8 Hz), 6.61(d, 1H, J=7.8 Hz), 6.91(d, 1H, J=5.1 Hz), 7.14(t, 1H, J=7.8 Hz), 7.51(d, 1H, J=5.1 Hz)

Reference Example 20

Methyl (Z)-3-(3-acetamidostyryl)-2-thiophenecarboxylate

Substantially the same procedure as in Reference Example 14 was repeated using methyl (Z)-3-(3-nitrostyryl)

-2-thiophenecarboxylate obtained in Reference Example 13 (3.51 g, 12.1 mmol), and also using acetic anhydride (3.43 ml, 36.3 mmol) instead of trimethylacetyl chloride, to give methyl (Z)-3-(3-acetamidostyryl)-2-thiophenecarboxylate (3.33 g, 2 steps, 91.3%).

$^1$H-NMR (DMSO-d$_6$) δ:2.06(s, 3H), 3.88(s, 3H), 6.77(d, 1H, J=5.3 Hz), 6.82(d, 1H, J=12.3 Hz), 6.88(br d, 1H, J=8.0 Hz), 7.09(d, 1H, J=12.3 Hz), 7.26(t, 1H, J=8.0 Hz), 7.48(br, 1H), 7.57(br d, 1H, J=8.0 Hz), 7.74(d, 1H, J=5.3 Hz), 9.96(br, 1H)

Reference Example 21

(Z)-3-(3-Acetamidostyryl)-2-thiophenecarboxylic acid

Substantially the same procedure as in Reference Example 16 was repeated using the methyl ester obtained in Reference Example 20(3.33 g, 11.1 mmol) to give (Z)-3-(3-acetamidostyryl)-2-thiphenecarboxylic acid (2.95 g, 92.9%).

$^1$H-NMR (DMSO-d$_6$) δ:2.05(s, 3H), 6.74(d, 1H, J=5.1 Hz), 6.77(d, 1H, J=11.9 Hz), 6.88(br d, 1H, J=7.8 Hz), 7.12(d, 1H, J=11.9 Hz), 7.25(t, 1H, J=7.8 Hz), 7.47(br, 1H), 7.57(br d, 1H, J=7.8 Hz), 7.66(d, 1H, J=5.1 Hz), 9.96(br, 1H)

Reference Example 22

7-Acetamido-10H-benzo[5,6]cyclohepta[1,2-b]thiophen-10-one [1]

9-Acetamido-10H-benzo[5,6]cyclohepta[1,2-b]thiophen-10-one [2]

Substantially the same procedure as in Reference Example 17 was repeated using the carboxylic acid obtained in Reference Example 21(2.80 g, 9.75 mmol) to give [1] (0.94 g, 42.9%) and [2] (0.78 g, 29.7%), respectively.

[1] $^1$H-NMR (DMSO-d$_6$) δ:2.21(s, 3H), 7.41(d, 1H, J=11.5 Hz), 7.51(d, 1H, J=11.5 Hz), 7.66(d, 1H, J=4.9 Hz), 7.99(dd, 1H, J=9.0, 2.0 Hz), 8.23(d, 1H, J=4.9 Hz), 8.25(d, 1H, J=2.0 Hz), 8.67(d, 1H, J=9.0 Hz), 10.59(d, 1H, J=8.6 Hz)

[2] $^1$H-NMR (CDCl$_3$) δ:2.31(s, 3H), 7.21(d, 1H, J=12.0 Hz), 7.30(d, 1H, J=12.0 Hz), 7.31(d, 1H, J=5.3 Hz), 7.45(dd, 1H, J=8.3, 0.7 Hz), 7.71(t, 1H, J=8.3 Hz), 7.79(d, 1H, J=5.3 Hz), 8.99(dd, 1H, J=8.3, 0.7 Hz), 12.87(br, 1H)

Reference Example 23

7-Amino-10H-benzo[5,6]cyclohepta(1,2-b]thiophen-10-one

Substantially the same procedure as in Reference Example 18 was repeated using 7-acetamido-10H-benzo[5,6]-cyclohepta[1,2-b]thiophen-10-one obtained in Reference Example 22 to give 7-amino-10H-benzo[5,6]cyclohepta[1,2-b]thiophen-10-one (87.2%).

$^1$H-NMR (CDCl$_3$) δ:6.86(d, 1H, J=2.3 Hz), 6.99(dd, 1H, J=8.9, 2.3 Hz), 7.08(d, 1H, J=11.6 Hz), 7.19(d, 1H, J=11.6 Hz), 7.30(d, 1H, J=5.3 Hz), 7.69(d, 1H, J=5.3 Hz), 8.71(d, 1H, J=8.9 Hz)

Reference Example 24

9-Amino-10H-benzo[5,6]cyclohepta[1,2-b]thiophen-10-one

Substantially the same procedure as in Reference Example 18 was repeated using 9-acetamido-10H-benzo[5, 6]-cyclohepta[1,2-b]thiophen-10-one obtained in Reference Example 22 to give 9-amino-10H-benzo[5,6]cyclohepta[1,2-b]thiophen-10-one (99.9%).

$^1$H-NMR (CDCl$_3$) δ:6.84(dd, 1H, J=7.9, 1.3 Hz), 6.92(br d, 1H, J=7.9 Hz), 6.97(d, 1H, J=11.7 Hz), 7.10(d, 1H, J=11.7 Hz), 7.20(d, 1H, J=5.1 Hz), 7.38(t, 1H, J=7.9 Hz), 7.66(d, 1H, J=5.1 Hz)

Reference Example 25

2-Acetamido-5H-dibenzo[a,d]cyclohepten-5-one

In a mixed solvent of carbon tetrachloride (45 ml) and chloroform (25 ml) was dissolved 2-acetamido-10,11-dihydro-5H-dibenzo[a,d]cyclohepten-5-one obtained substantially in the same manner as in Reference Examples 12 to 17(2.60 g, 9.80 mmol), and NBS (1.92 g, 10.8 mmol) and AIBN (0.6 g) were added thereto, followed by heating under reflux for 5 hours. The reaction mixture was washed successively with water and a saturated aqueous solution of sodium chloride, and then dried over anhydrous magnesium sulfate. After the drying agent was filtered off, the organic layer was concentrated under reduced pressure. The obtained residue was dissolved in dimethylformamide (100 ml), and DBU (2.60 ml) was added thereto, followed by stirring at 60° C. for 2 hours. The reaction mixture was poured into ice-an aqueous solution of ammonium chloride, followed by extraction with ethyl acetate. The organic layer was washed successively with water and a saturated aqueous solution of sodium chloride, and then dried over anhydrous magnesium sulfate. After the drying agent was filtered off, the organic layer was concentrated under reduced pressure. The obtained residue was triturated with diisopropyl ether to give 2-acetamido-5H-dibenzo[a,d]cyclohepten-5-one (0.97 g, 37.6%).

$^1$H-NMR (DMSO-d$_6$) δ:2.18(s, 3H), 7.18(d, 1H, J=12.2 Hz), 7.28(d, 1H, J=12.2 Hz), 7.63–7.74(m, 1H), 7.77–7.86 (m, 3H), 8.02(d, 1H, J=2.0 Hz), 8.13–8.22(m, 2H), 10.47(br, 1H)

Reference Example 26

2-Amino-5H-dibenzo[a,d]cyclohepten-5-one

Substantially the same procedure as in Reference Example 18 was repeated using 2-acetamido-5H-dibenzo[a, d]-cyclohepten-5-one obtained in Reference Example 25(0.70 g, 2.66 mmol) to give 2-amino-5H-dibenzo[a,d]cyclohepten-5-one (0.59 g, 99.9%).

$^1$H-NMR (CDCl$_3$) δ:4.13(br, 2H), 6.71(d, 1H, J=2.7 Hz), 6.83(dd, 1H, J=8.6, 2.7 Hz), 6.89(d, 1H, J=12.2 Hz), 7.00(d, 1H, J=12.2 Hz), 7.48–7.65(m, 3H), 8.19(d, 1H, J=8.6 Hz), 8.24–8.34(m, 1H

Reference Example 27

(S)-3,3,3-Trifluoro-2-hydroxy-2-methylpropionic acid

To a solution of 3,3,3-trifluoro-2-hydroxy-2-methylpropionic acid (13.0 g, 82.3 mmol) in ethanol (60 ml) was added dropwise (S)-(−)-1-phenylethylamine (9.97 g, 82.3 mmol) at 0° C., followed by stirring at room temperature for one hour. The resulting mixture was concentrated under reduced pressure to give a salt as white crystals. This salt was recrystallized from a10% butanol/toluene solution (60 ml) six times to give S-form of 3,3,3-trifluoro-2-hydroxy-2-methylpropionic acid phenylethylamine salt {(S, S) salt} (3.85 g, 13.8 mmol, 97% e.e.). The optical purity was determined with ¹H-NMR. The obtained {(S,S) salt} was dissolved in 2N hydrochloric acid, and diethyl ether was added thereto, followed by stirring at room temperature for one hour. The organic layer was washed successively with water and a saturated aqueous solution of sodium chloride, and then dried over anhydrous sodium sulfate. After the drying agent was filtered off, the organic layer was concentrated under reduced pressure to give (S)-3,3,3-trifluoro-2-hydroxy-2-methylpropionic acid as white crystals (2.13 g, 13.5 mmol).

¹H-NMR (CDCl₃) δ:1.65(s, 3H) Melting point:102°–104° C.

Reference Example 28

(R)-3,3,3-Trifluoro-2-hydroxy-2-methylpropionic acid

Substantially the same procedure as in Reference Example 27 was repeated using (R)-(-)-1-phenylethylamine instead of (S)-(-)-1-phenylethylamine to give (R)-3,3,3-trifluoro-2-hydroxy-2-methylpropionic acid.

¹H-NMR (CDCl₃) δ:1.65(s, 3H) Melting point:101°–105° C.

INDUSTRIAL APPLICABILITY

The present invention provides tricyclic compounds which are useful as therapeutic agents for urinary incontinence.

We claim:

1. A tricyclic compound represented by general formula

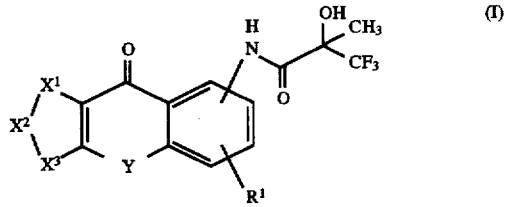

wherein $R^1$ represents hydrogen, lower alkyl, lower alkoxy, or halogen; $-X^1-X^2-X^3-$ represents $-CR^2=CR^3-S-$ (wherein $R^2$ and $R^3$ are independently hydrogen, lower alkyl, lower alkoxy or halogen), $-CR^2=CR^3-O-$, $-S-CR^4=CR^5-$ (wherein $R^4$ and $R^5$ are independently hydrogen, lower alkyl, lower alkoxy or halogen), or $-O-CR^4=CR^5-$; and Y represents $-CH_2O-$.

2. A tricyclic compound according to claim 1, wherein $-X^1-X^2-X^3-$ is $-CR^2=CR^3-S-$ or $-CR^2=CR^3-O-$.

3. A tricyclic compound according to claim 1, wherein $-X^1-X^2-X^3-$ is $-S-CR^4=CR^5-$ or $-O-CR^4=CR^5-$.

* * * * *